(12) United States Patent
Miyayashiki

(10) Patent No.: US 9,118,818 B2
(45) Date of Patent: Aug. 25, 2015

(54) ENDOSCOPE APPARATUS, REPRODUCING APPARATUS, DISPLAYING METHOD AND INSPECTION REPORT GENERATING APPARATUS

(75) Inventor: Hidehiro Miyayashiki, Akishima (JP)

(73) Assignee: OLYMPUS CORPORATION, Tokyo (JP)

(*) Notice: Subject to any disclaimer, the term of this patent is extended or adjusted under 35 U.S.C. 154(b) by 495 days.

(21) Appl. No.: 13/533,654

(22) Filed: Jun. 26, 2012

(65) Prior Publication Data

US 2013/0342667 A1 Dec. 26, 2013

(51) Int. Cl.
| H04N 7/18 | (2006.01) |
| A61B 1/00 | (2006.01) |
| A61B 1/05 | (2006.01) |
| G02B 23/24 | (2006.01) |
| H04N 5/765 | (2006.01) |
| H04N 5/225 | (2006.01) |

(52) U.S. Cl.
CPC .............. *H04N 7/185* (2013.01); *A61B 1/0005* (2013.01); *A61B 1/0008* (2013.01); *A61B 1/00009* (2013.01); *A61B 1/05* (2013.01); *G02B 23/2484* (2013.01); *H04N 5/765* (2013.01); *H04N 2005/2255* (2013.01)

(58) Field of Classification Search
CPC .......... H04N 5/765; H04N 2005/2255; H04N 7/185; A61B 1/00009; A61B 1/0005; A61B 1/0008; G02B 23/2484
USPC .......................................................... 348/65
See application file for complete search history.

(56) References Cited

U.S. PATENT DOCUMENTS

| 5,899,851 | A | * | 5/1999 | Koninckx | 600/117 |
| 8,013,925 | B2 | | 9/2011 | Ito | |
| 8,081,208 | B2 | | 12/2011 | Inomata et al. | |
| 2002/0161280 | A1 | * | 10/2002 | Chatenever et al. | 600/112 |
| 2005/0272971 | A1 | * | 12/2005 | Ohnishi et al. | 600/101 |
| 2006/0084840 | A1 | * | 4/2006 | Hoeg et al. | 600/117 |
| 2009/0135249 | A1 | * | 5/2009 | Hirakawa | 348/74 |
| 2010/0277617 | A1 | * | 11/2010 | Hollinger | 348/231.99 |

FOREIGN PATENT DOCUMENTS

| JP | 11-281897 A | 10/1999 |
| JP | 2002-263057 A | 9/2002 |
| JP | 2003-093326 A | 4/2003 |
| JP | 2008-301332 A | 12/2008 |
| WO | WO 2007/063680 A1 | 6/2007 |

OTHER PUBLICATIONS

Tanaka, Hideki, JP 2007-054401, Mar. 8, 2007, [0004], [0032], [0045], [0051], [0055], [0073]-[0074] and fig. 5.*
Japanese Office Action dated Mar. 4, 2014 in counterpart Japanese Application No. 2010-149973.

* cited by examiner

*Primary Examiner* — Christopher S Kelley
*Assistant Examiner* — Matthew Kwan
(74) *Attorney, Agent, or Firm* — Holtz, Holtz, Goodman & Chick PC

(57) ABSTRACT

An endoscope apparatus includes: an image processing portion that performs image processing on a signal of an image picked up by an image pickup device provided at a distal end portion of an endoscope insertion portion to generate an endoscope image; a gravity direction detecting portion that detects information about a gravity direction of the distal end portion; a gravity signal processing portion that performs predetermined signal processing on a signal of the information about the gravity direction detected by the gravity direction detecting portion to detect gravity information. The recording medium reading/writing portion of the endoscope apparatus stores data of the endoscope image generated by the image processing portion and data of the gravity information detected by the gravity signal processing portion in two AVI files and records the files on a recording medium.

6 Claims, 31 Drawing Sheets

FIG.3A     FIG.3B     FIG.3C
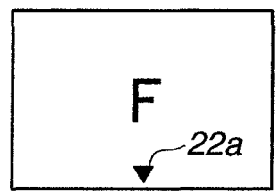
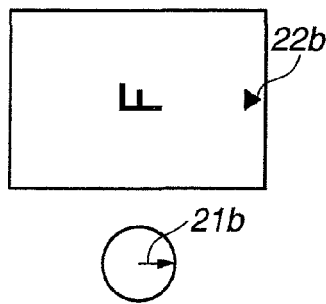
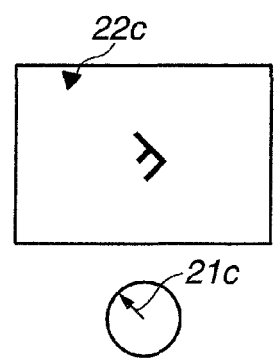
GRAVITY DIRECTION:
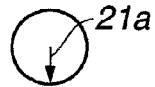     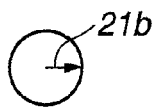     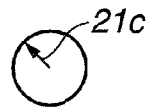

FIG.4

| STRUCTURE | | | | DATA | COMMENT |
|---|---|---|---|---|---|
| RIFF "AVI" | | | | "RIFF" | |
| | LIST "hdrl" | | | "LIST" | |
| | | avih | | "avih" | AVI MAIN HEADER |
| | | LIST "strl" | | "LIST" | |
| | | LIST "strl" | | "LIST" | |
| | | | strh | "strh" | AVI STREAM HEADER |
| | | | strf | "strf" | STREAM FORMAT |
| | | | strn | "strn" | OPTION DATA |
| | | | | ***** | SIZE |
| | | | | ⋮ | FOLLOWED BY OPTION DATA CONTENT |
| | | | | | ADDITION INFORMATION FLAG |
| | JUNK | | | "JUNK" | DUMMY CHUNK TO ACHIEVE 2048-BYTE BOUNDARY |
| | LIST "movi" | | | "LIST" | |
| | | 00dc (JPEG DATA) #01 | | "00dc" | |
| | | | | ***** | SIZE |
| | | | | %%%%% | FRAME DATA |
| | | ⋮ | | ⋮ | ⋮ |
| | | 00dc (JPEG DATA) #30 | | "00dc" | |
| | | | | ***** | SIZE |
| | | | | %%%%% | FRAME DATA |
| | | 01wb (WAVE DATA) #01 | | "01wb" | |
| | | | | ***** | SIZE |
| | | | | %%%%% | FRAME DATA |
| | | 01wb (ADDITION INFORMATION DATA) #01 | | "02hm" | |
| | | | | ***** | SIZE |
| | | | | %%%%% | DATA |
| | | 00dc (JPEG DATA) #31 | | "00dc" | |
| | | | | ***** | SIZE |
| | | | | %%%%% | FRAME DATA |
| | | ⋮ | | ⋮ | ⋮ |
| | | 00dc (JPEG DATA) #60 | | "00dc" | |
| | | | | ***** | SIZE |
| | | | | %%%%% | FRAME DATA |
| | | 01wb (WAVE DATA) #02 | | "01wb" | |
| | | | | ***** | SIZE |
| | | | | %%%%% | FRAME DATA |
| | | 01wb (ADDITION INFORMATION DATA) #02 | | "02hm" | |
| | | | | ***** | SIZE |
| | | | | %%%%% | DATA |
| | | ⋮ | | ⋮ | |
| | idx1 | | | "idx1" | INDEX TO INDICATE REPRODUCING ORDER |

FIG.17A  FIG.17B  FIG.17C
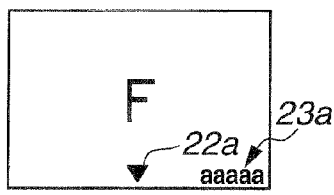 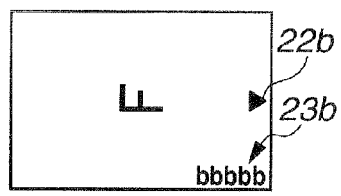 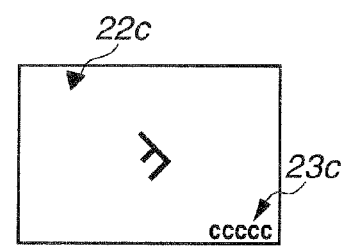
GRAVITY
DIRECTION: 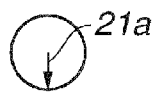 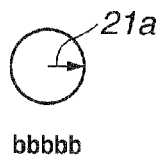 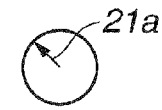
INSERTION
LENGTH:  aaaaa  bbbbb  ccccc FIG.24
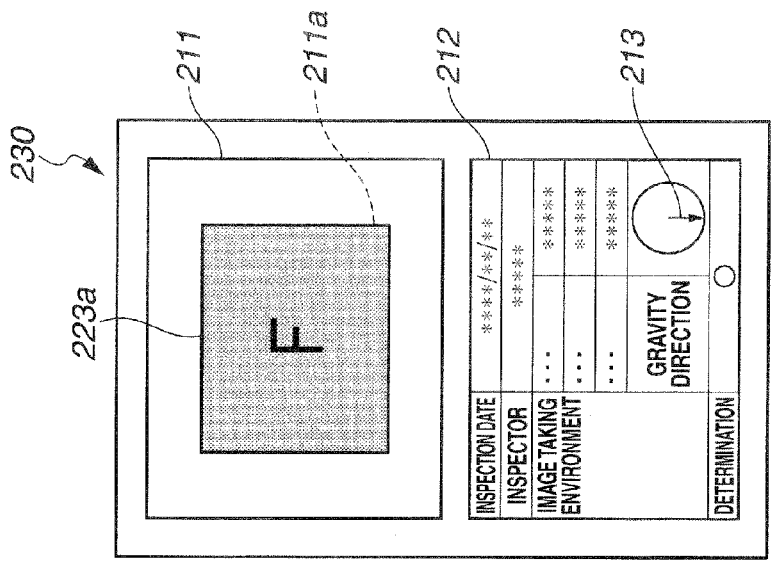
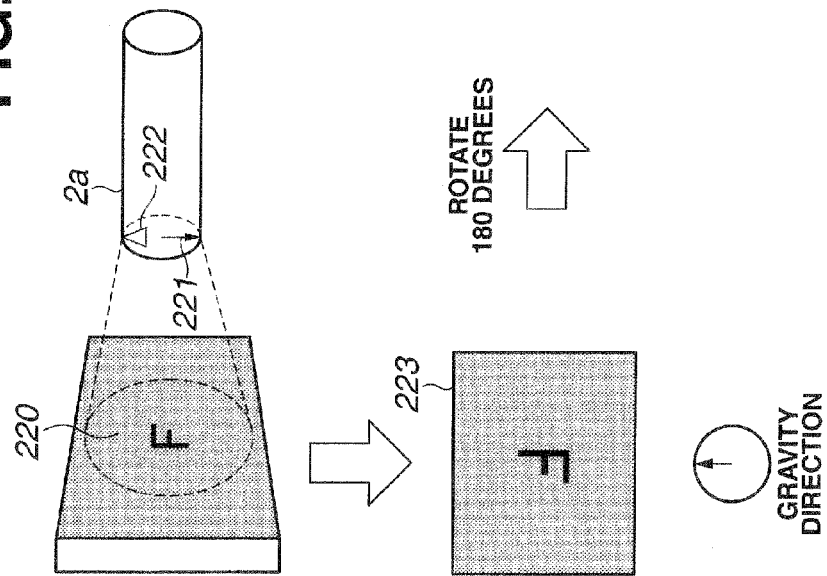

ENDOSCOPE APPARATUS, REPRODUCING APPARATUS, DISPLAYING METHOD AND INSPECTION REPORT GENERATING APPARATUS

BACKGROUND OF THE INVENTION

1. Field of the Invention

The present invention relates to an endoscope apparatus, a reproducing apparatus, a displaying method and an inspection report generating apparatus, and more particularly, to an endoscope apparatus which can detect an endoscope image and gravity information, a reproducing apparatus, a displaying method and an inspection report generating apparatus.

2. Description of the Related Art

Conventionally, typically used endoscope apparatuses each include an endoscope for obtaining an observed image by inserting an insertion portion into a site to be observed and display means for displaying the observed image.

In such an endoscope apparatus, since an inspector can perform an inspection while observing an observed image, namely, an endoscope image displayed on display means such as a monitor when an insertion portion of an endoscope is inserted in a site to be observed, the inspector does not feel strange in an inspection and can reliably recognize a desired observed image by displaying the image on a monitor or the like.

Also, an endoscope apparatus with a gravity sensor provided with a distal end of an insertion portion is proposed which notifies an inspector of a gravity direction of an observed image displayed on a monitor by superimposing on an endoscope image a detection result of the gravity direction from the gravity sensor (e.g., see Japanese Patent Application Laid-Open Publication No. 2002-263057).

SUMMARY OF THE INVENTION

An endoscope apparatus according to an aspect of the present invention includes: an image processing portion that performs image processing on a signal of an image picked up by an image pickup device provided at a distal end portion of an endoscope insertion portion to generate an endoscope image; a gravity direction detecting portion that detects information about a gravity direction of the distal end portion; a gravity signal processing portion that performs predetermined signal processing on a signal of the information about the gravity direction detected by the gravity direction detecting portion to detect gravity information; and a recording medium reading/writing portion to and from which a recording medium is attachable and detachable and that stores data of the endoscope image and data of the gravity information in one moving image file and records the file on the recording medium.

BRIEF DESCRIPTION OF THE DRAWINGS

FIGS. 3A to 3C are diagrams showing examples of a display screen on which gravity information is displayed;

FIG. 4 is a diagram for illustrating an example of structure of an AVI file;

FIGS. 17A to 17C are diagrams showing examples of a display screen on which gravity information and insertion length information are displayed;

FIG. 24 is a diagram for illustrating still another example of the inspection image rotating process;

DETAILED DESCRIPTION OF THE PREFERRED EMBODIMENTS

Embodiments of the present invention will now be described in detail with reference to the drawings.

First Embodiment

First, a configuration of an endoscope apparatus according to a first embodiment will be described based on FIG. 1 and FIG. 2.

Figure 1:
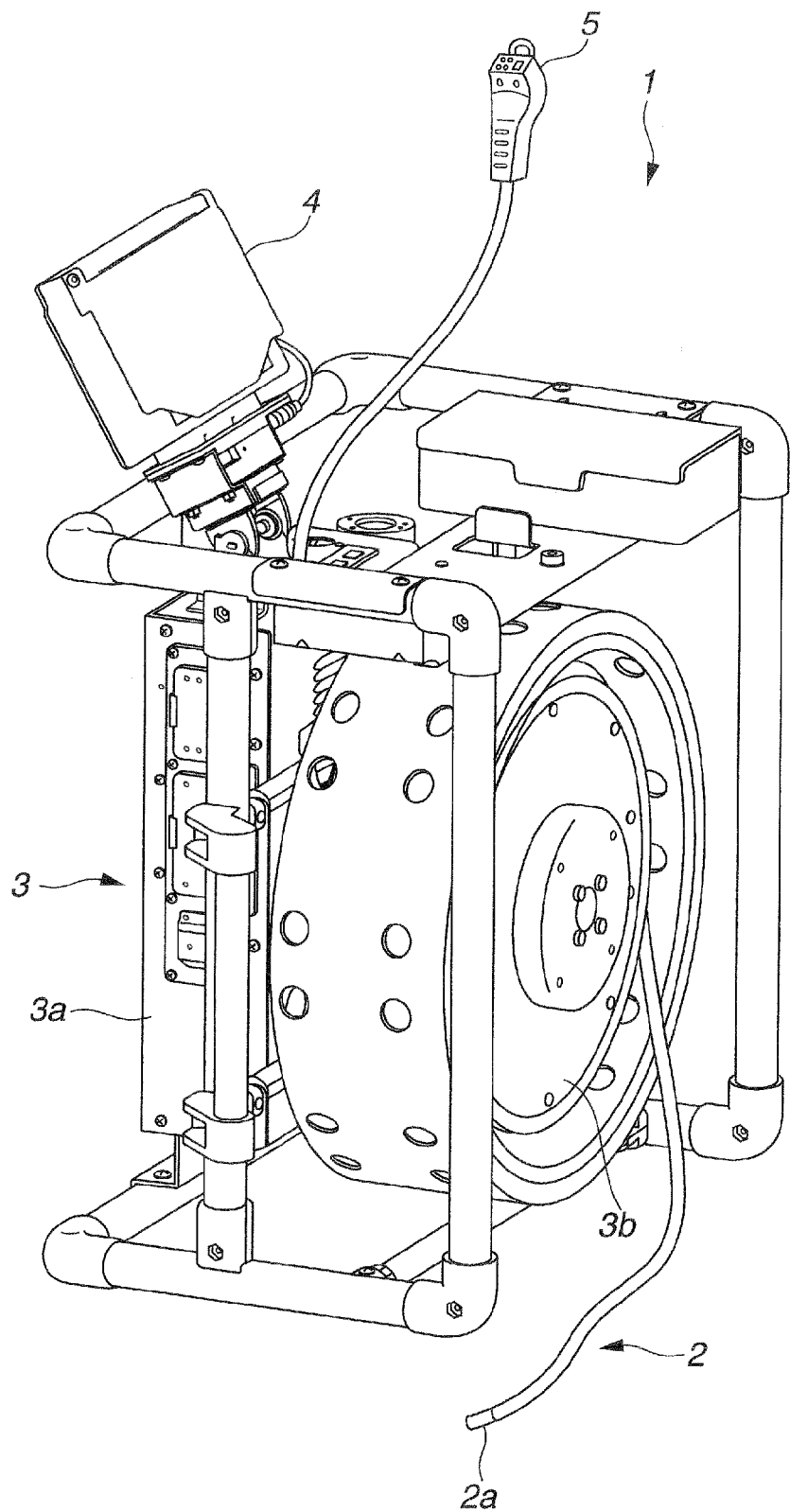
FIG. 1 is a perspective view showing an entire configuration of an endoscope apparatus according to a first embodiment.
Figure 2:
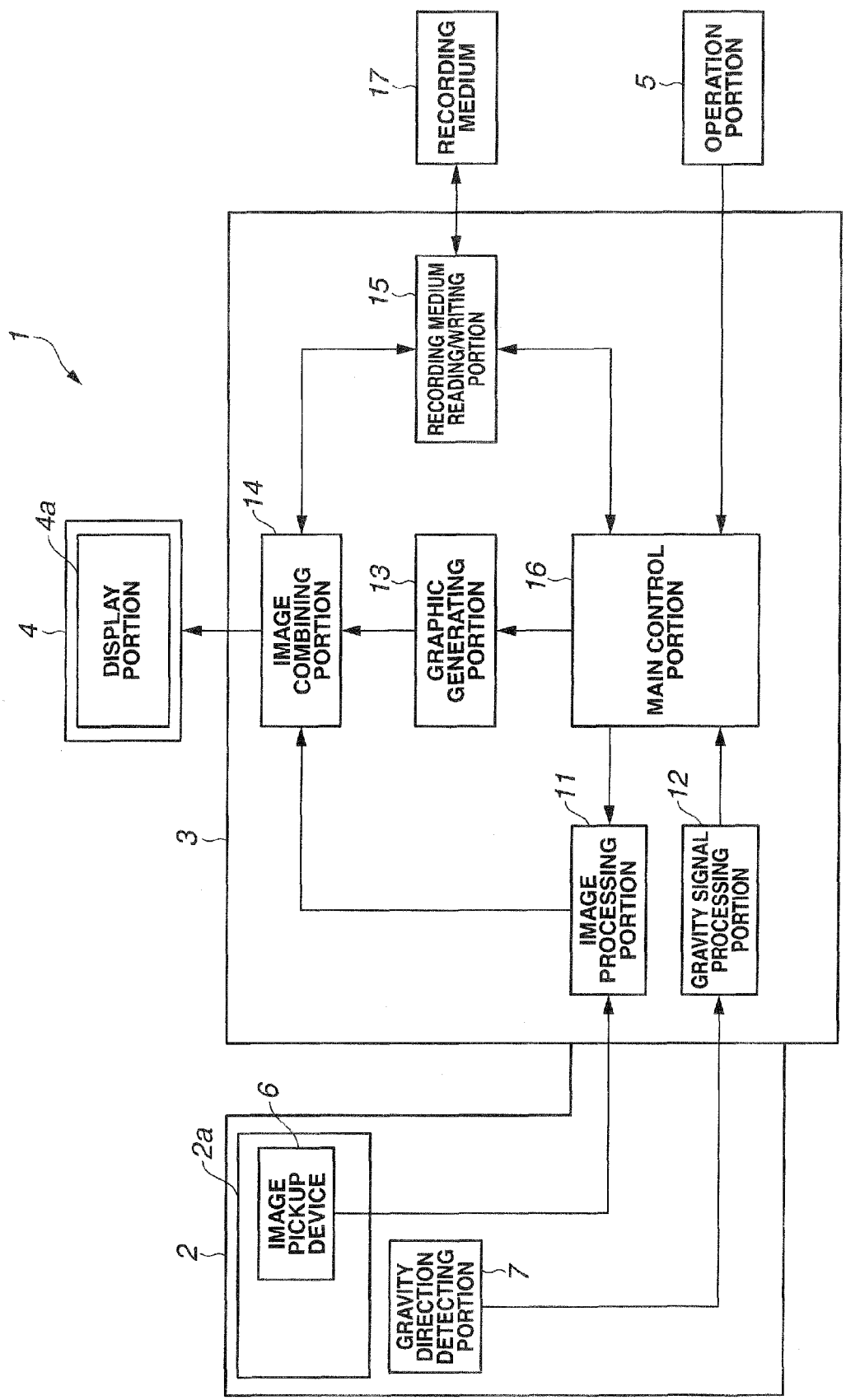
FIG. 2 is a block diagram showing the entire configuration of the endoscope apparatus according to the first embodiment.

FIG. 1 is a perspective view showing an entire configuration of the endoscope apparatus according to the first embodiment, and FIG. 2 is a block diagram showing the entire configuration of the endoscope apparatus according to the first embodiment.

As shown in FIG. 1, an endoscope apparatus 1 of the present embodiment includes a long-length insertion portion 2 with a distal end portion 2a, a main body portion 3 having a pivotably installed drum portion 3a which is a swivel portion for reeling up the insertion portion 2 and a box-shaped fixing portion 3b to which the drum portion 3a is rotatably connected, a display device 4 which is installed on top of the main body portion 3 and erectable, and an operation portion 5 for performing moving image recording and the like described later.

An inspector inserts the insertion portion 2 as an endoscope insertion portion into an object to be checked such as a pipe. Then, the inspector accesses a desired check portion while watching an endoscope image displayed on a display portion 4a of the display device 4 shown in FIG. 2, and performs an inspection and a diagnostic operation with the endoscope image.

As shown in FIG. 2, the distal end portion 2a includes an image pickup device 6 such as a CCD that generates an image pickup signal by photoelectric conversion of an object image. Also, the insertion portion 2 includes a gravity direction detecting portion 7 in the vicinity of a proximal end of the distal end portion 2a. The gravity direction detecting portion 7 detects information about a gravity direction of the distal end portion 2a.

The gravity direction detecting portion 7 is, for example, a gravity sensor and outputs to the main body portion 3 a signal depending upon the detected information about the gravity direction of the distal end portion 2a, namely, a signal of the information about the gravity direction of the distal end portion 2a.

The main body portion 3 includes an image processing portion 11, a gravity signal processing portion 12, a graphic generating portion 13, an image combining portion 14, a recording medium reading/writing portion 15, and a main control portion 16.

The image processing portion 11 receives image pickup signals (as input) outputted from the image pickup device 6 incorporated in the distal end portion 2a of the insertion portion 2. The image processing portion 11 performs image processing on the image pickup signals, such as gamma correction processing, edge enhancement processing and digital zoom processing to generate an endoscope image. The image processing portion 11 supplies the generated endoscope image to the image combining portion 14.

The gravity signal processing portion 12 receives information signals (as input) about a gravity direction of the distal end portion 2a outputted from the gravity direction detecting portion 7. The gravity signal processing portion 12 converts the information signals into gravity information such as an inclination angle with respect to a perpendicularly downward direction, and supplies the converted gravity information to the main control portion 16.

The gravity information is supplied from the main control portion 16 to the graphic generating portion 13. The graphic generating portion 13 generates an indicator indicating the gravity direction based on the gravity information supplied from the main control portion 16 and supplies the generated indicator to the image combining portion 14.

The image combining portion 14 combines the endoscope image supplied from the image processing portion 11 with the indicator supplied from the graphic generating portion 13 into one sheet of video data and outputs the combined image to the display device 4. As a result, the combined image is displayed on the display portion 4a of the display device 4.

Also, the image combining portion 14 may perform processing to display an endoscope image independently on the display portion 4a of the display device 4 in response to control by the main control portion 16. Thus, images such as an endoscope image or a combined image of an endoscope image and an indicator are displayed on the display portion 4a of the display device 4.

A recording medium 17 such as a flash memory card is attachable and detachable to and from the recording medium reading/writing portion 15. With the recording medium 17 mounted in the recording medium reading/writing portion 15, if the inspector operates the operation portion 5 to give an instruction to perform a recording operation, in accordance with control by the main control portion 16, the recording medium reading/writing portion 15 retrieves endoscope image data and gravity information data supplied to the image combining portion 14 and supplies the data to the recording medium 17. Thus, the data is recorded on the recording medium 17. In such recording processing, the recording medium reading/writing portion 15 records endoscope image data and gravity information data in the recording medium 17 as one moving image file such as an AVI file.

Also, the recording medium reading/writing portion 15 can retrieve endoscope image data and gravity information data recorded in the recording medium 17 in accordance with control by the main control portion 16. At this time, the recording medium reading/writing portion 15 supplies endoscope image data to the image combining portion 14 and gravity information data to the main control portion 16. The gravity information data supplied to the main control portion 16 is supplied to the graphic generating portion 13, and an indicator indicating the gravity direction is generated. The indicator indicating the gravity direction is supplied to the image combining portion 14, and a combined image of the endoscope image and the indicator is generated. Then, the combined image is displayed on the display portion 4a of the display device 4.

The operation portion 5 is provided with operation switches (not shown) for performing a bending operation of the distal end portion 2a and a recording operation into the above-described recording medium 17. The inspector operates the operation switches of the operation portion 5 to perform desired operations such as the bending operation, the recording operation, and the like. The operation portion 5 supplies the main control portion 16 with operation signals corresponding to the inspector's operation.

The main control portion 16 controls circuit portions so as to perform processing corresponding to operation signals from the operation portion 5, and controls the operations of the entire endoscope apparatus 1.

Now, a display screen displayed on the display portion 4*a* of the display device 4 will be described.

FIGS. 3A to 3C are diagrams showing examples of a display screen on which gravity information is displayed. In FIG. 3A to FIG. 3C, an object is illustrated by a character "F." Also, in FIG. 3A to FIG. 3C, arrows 21*a* to 21*c* indicate the gravity directions detected by the gravity direction detecting portion 7.

As indicated by the arrow 21*a* in FIG. 3A, if the gravity direction detected by the gravity direction detecting portion 7 is downward viewed from the front of FIG. 3A, the graphic generating portion 13 generates an indicator 22*a* indicating that the gravity direction is downward. Then, the indicator 22*a* is combined in the lower part of an endoscope image by the image combining portion 14 and displayed on the display portion 4*a* of the display device 4.

Also, as indicated by the arrow 21*b* in FIG. 3B, if the gravity direction detected by the gravity direction detecting portion 7 is rightward viewed from the front of FIG. 3B, the graphic generating portion 13 generates an indicator 22*b* indicating that the gravity direction is rightward. Then, the indicator 22*b* is combined on the right side of an endoscope image by the image combining portion 14 and displayed on the display portion 4*a* of the display device 4.

Further, as indicated by the arrow 21*c* in FIG. 3C, if the gravity direction detected by the gravity direction detecting portion 7 is obliquely upward to the left viewed from the front of FIG. 3C, the graphic generating portion 13 generates an indicator 22*c* indicating that the gravity direction is obliquely upward to the left. Then, the indicator 22*c* is combined in the upper left of an endoscope image by the image combining portion 14 and displayed on the display portion 4*a* of the display device 4.

Next, structure of an AVI file recorded on the recording medium 17 will be described.

FIG. 4 is a diagram for illustrating an example of the structure of an AVI file.

As shown in FIG. 4, an AVI file 30 has a format of RIFF (resource interchange file format) and a structure including a header portion 31 denoted by LIST "hdrl," a dummy chunk 32 denoted by JUNK, a stream data portion 33 denoted by LIST "movi," and an index 34 denoted by idx1 in this order from a head of the file.

The header portion 31 has a structure including an AVI main header 35 denoted by Avih, a stream list for moving image data 36 denoted by LIST "strl," and a stream list for audio data 37 denoted by LIST "strl."

The stream list for audio data 37 has a structure including an AVI stream header 38 denoted by strh, a stream format 39 denoted by strf, and an option data 40 denoted by strn.

In the present embodiment, an addition information flag is added to option data content of the option data 40 of the header portion 31. This addition information flag is a flag that indicates whether or not gravity information data is stored in the AVI file 30. If gravity information data is not stored in the AVI file 30, flag information on the addition information flag is set to 0. If gravity information data is stored in the AVI file 30, flag information on the addition information flag is set to 1. The flag information on the addition information flag is set by the recording medium reading/writing portion 15 in accordance with the control by the main control portion 16.

Also, the stream data portion 33 has a structure including a plurality of, here, two items of stream data 33*a* and 33*b* divided by unit time. It should be noted that although only the two items of the stream data 33*a* and 33*b* are shown in FIG. 4, stream data items depending on a moving image taking time are stored in the stream data portion 33. Specifically, if a 60-sec moving image is recorded on the AVI file 30, the stream data portion 33 has 60 items of stream data. It should be noted that since configurations of the stream data items are identical to each other, hereinafter, a configuration of the stream data 33*a* will be described by way of example.

The stream data 33*a* as a stream data region is composed of 30 image streams 41*a* as image storage and one voice stream 42*a*. Further, if gravity information is added, a region of an information stream 43*a* as information storage is reserved. Then, if the gravity information is added, gravity information data is stored in the region of the information stream 43*a*. In the image streams 41*a*, endoscope image data is stored. In the voice stream 42*a*, voice information data associated with the endoscope image data is stored. In the information stream 43*a*, gravity information data associated with the endoscope image data is stored.

It should be noted that the 30 image streams 41*a* are stored in the stream data 33*a* per unit time; in other words, although a frame rate has been set at 30, 30 fps is not restrictive and the frame rate may also be 24, for example.

Also, if voice recording is not performed, the region of the voice stream 42*a* may not be provided. Alternatively, gravity information may be stored in the region of the voice stream 42*a* and the information stream 43*a* may not be provided. As a result, file size of the AVI file 30 may be reduced.

Also, although the one information stream 43*a* is provided in the stream data 33*a*, two or more information streams may also be provided. For example, 30 information streams each corresponding to the 30 image streams 41*a* are provided in the stream data 33*a* per unit time. Then, each of gravity information items corresponding to the 30 image streams 41*a* is stored in each region of the 30 information streams. As a result, since the 30 gravity information items corresponding to the 30 frame data items are displayed, precise gravity information can be displayed.

Also, in the present embodiment, data of an endoscope image and a gravity direction is stored in the single AVI file 30. For example, in the case where there are a large number of moving image files, if endoscope image data and gravity direction data are saved in different files, copying and moving the files are bothersome. Also, in the case where there are a large number of moving image files, if endoscope image data and gravity direction data are saved in different files, failures of copying and moving the files may occur. Specifically, if any one of the file of endoscope image data and the file of gravity direction data is failed to be copied, a detailed inspection is not be allowed. In contrast, in the present embodiment, since data of an endoscope image and a gravity direction is recorded in the single AVI file 30, a failure of copying a file is prevented and file management is easy.

It should be noted that a form of a moving image file is not limited to the AVI file 30, and an MOV file may be adopted. An MOV file is constituted by tracks and may include a text track, a chapter track and the like in addition to a moving image track and a voice track. For example, gravity information data may be recorded on the text track or the chapter track.

Although the AVI file 30 recorded on the recording medium 17 may be reproduced in the endoscope apparatus 1 as described above, if the inspector brings the recording medium 17 back to an office or the like to perform a detailed inspection, it is troublesome to carry also the heavy endoscope apparatus 1. Thus, the inspector brings only the recording medium 17 back to an office or the like and performs a detailed inspection by using a reproducing apparatus shown in FIG. 5 to reproduce the AVI file 30 recorded on the recording medium 17 as well as the inspector can draw up an inspection report depending on a result of the detailed inspection.

Figure 5:
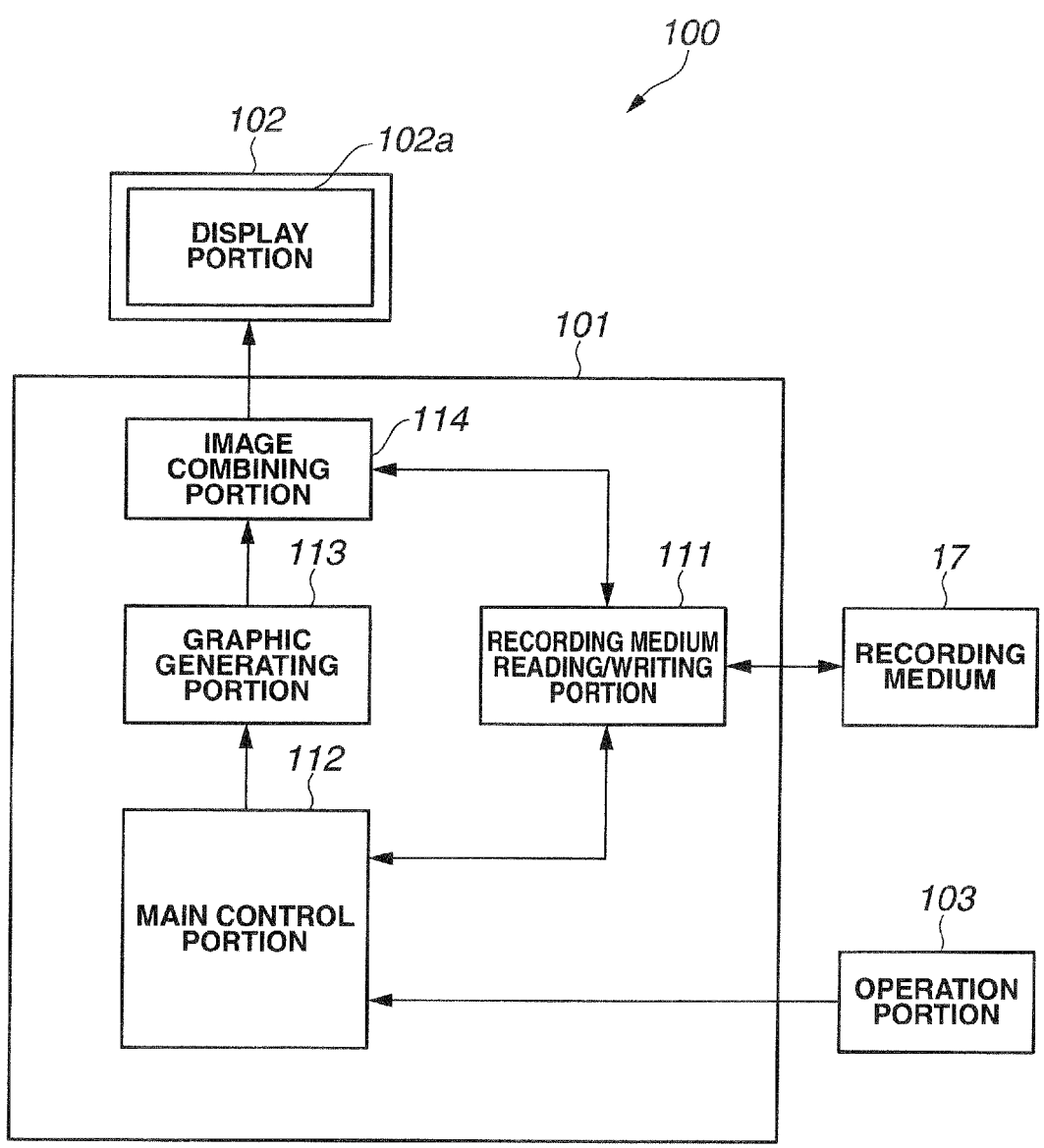
FIG. 5 is a block diagram showing an example of a configuration of a reproducing apparatus that reproduces an AVI file.

FIG. 5 is a block diagram showing an example of a configuration of the reproducing apparatus that reproduces an AVI file.

A reproducing apparatus 100 is, for example, a personal computer and includes a main body portion 101, a display device 102 having a display portion 102a such as an LCD, and an operation portion 103 such as a keyboard or a mouse for performing various operations.

The main body portion 101 includes a recording medium reading/writing portion 111, a main control portion 112, a graphic generating portion 113, and an image combining portion 114.

If the inspector makes an instruction to perform reproduction processing using the operation portion 103, an operation signal of this is supplied to the main control portion 112. The main control portion 112 instructs the recording medium reading/writing portion 111 to retrieve data recorded in the AVI file 30 in response to the operation signal. The recording medium reading/writing portion 111 retrieves the AVI file 30 recorded on the mounted recording medium 17 in accordance with control by the main control portion 112.

The main control portion 112 detects an addition information flag stored in the header portion 31 of the read AVI file 30. If the detected addition information flag is 0, the main control portion 112 performs normal moving image reproducing, here, image and voice reproducing.

Also, if the detected addition information flag is 1, the main control portion 112 performs moving image reproducing with addition information, here, a gravity direction added. If moving image reproducing with a gravity direction added is performed, the recording medium reading/writing portion 111 supplies endoscope image data to the image combining portion 114 and gravity information data to the main control portion 112. The main control portion 112 supplies the supplied gravity information data to the graphic generating portion 113. The graphic generating portion 113 generates an indicator indicating the gravity direction of the distal end portion 2a based on the supplied gravity information data and outputs the generated indicator to the image combining portion 114.

The image combining portion 114 combines the indicator indicating the gravity direction with the endoscope image data and outputs the resultant data to the display device 102. Accordingly, the inspector can bring moving image data back from an inspection field, thereby reproducing the moving image data to perform a detailed inspection. Specifically, an endoscope image with gravity information as shown in FIG. 3A to FIG. 3C is displayed on the display portion 102a of the display device 102. In this manner, the inspector can reproduce the AVI file 30 recorded on the recording medium 17 using the reproducing apparatus 100 and draw up an inspection report including gravity information while viewing an endoscope image displayed on the display portion 102a of the display device 102.

Figure 6:
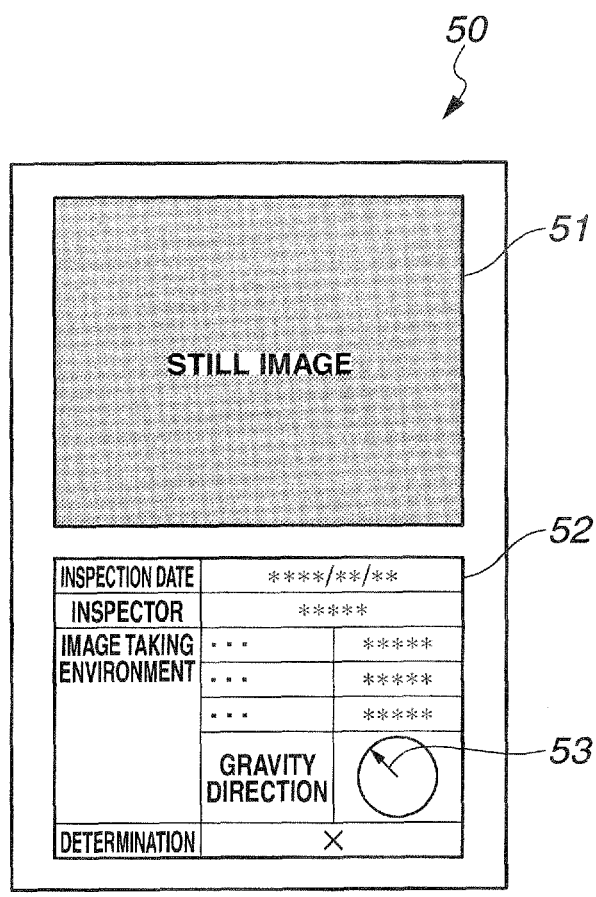
FIG. 6 is a diagram showing an example of an inspection report drawn up by an inspector.

FIG. 6 is a diagram showing an example of an inspection report drawn up by the inspector.

An inspection report 50 includes an image recording area 51 and an inspection condition input area 52. When the inspector uses the reproducing apparatus 100 to reproduce the AVI file 30 recorded on the recording medium 17 and performs a detailed inspection, if the inspector finds a flaw in an object as a result, then the inspector pastes the endoscope image at this time on the image recording area 51.

The inspection condition input area 52 has blanks for items of inspection date, inspector, image taking environment, and determination, as inspection conditions. The inspector fills in corresponding blanks with inspection conditions of an object under which a flaw is found. Also the inspector checks gravity information, namely, an indicator superimposed on an endoscope image when the flaw is found in the object and fills in a blank item of the image taking environment with the gravity direction. When the inspector finds a flaw in the object, if, for example, the inspector sees the indicator 22c shown in FIG. 3C, the inspector records an arrow 53 pointing obliquely upward to the left in the inspection report 50 as a gravity direction. It should be noted that an indication of the gravity direction is not limited to an arrow, and a text or the like may also be used.

Next, a process of displaying, as a list (as thumbnails), a plurality of moving image frames of which the AVI file 30 recorded on the recording medium 17 is composed will be described. It should be noted that the plurality of images displayed as thumbnails are not limited to moving image frames in the AVI file 30 (moving image file). The images may be a plurality of images (still images) recorded on the recording medium 17.

First, a process of displaying a plurality of recorded images as a list will be described. The process is executed by the main control portion 112, and thereby a plurality of images are displayed as a list on the display portion 102a.

Figure 7:
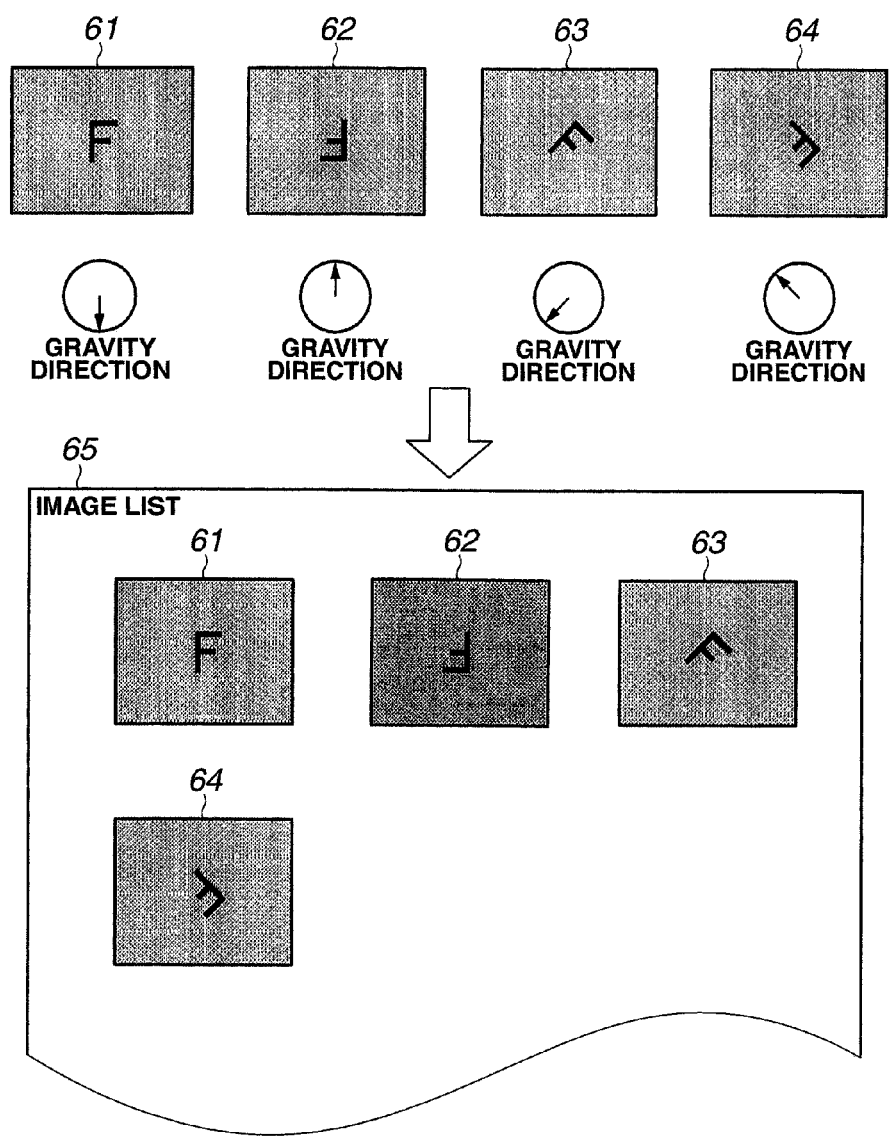
FIG. 7 is a diagram for illustrating an example of recorded images displayed as a list according to a conventional art.
Figure 8:
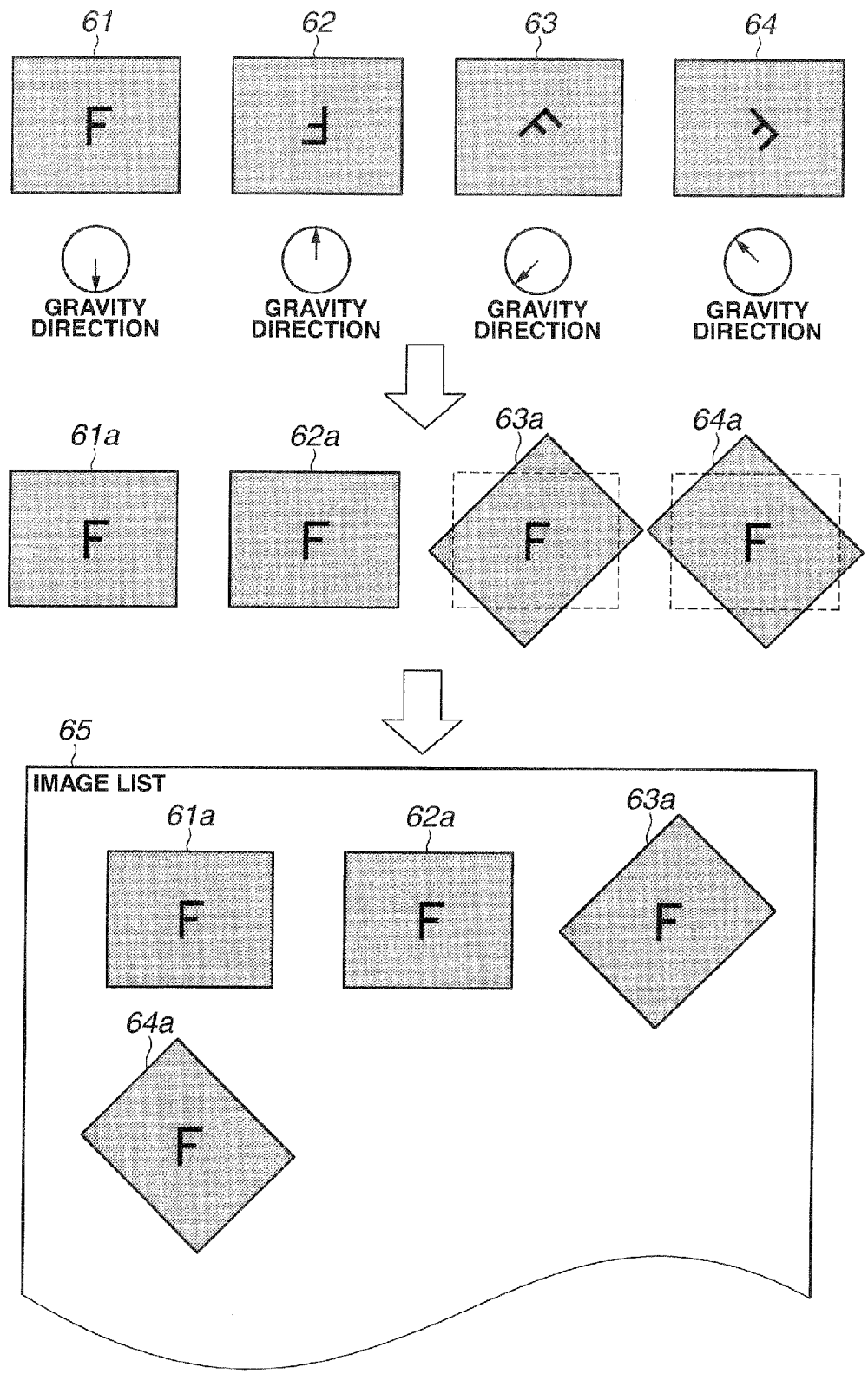
FIG. 8 is a diagram for illustrating an example of recorded images displayed as a list according to the present embodiment.

FIG. 7 is a diagram for illustrating an example of recorded images displayed as a list according to a conventional art, and FIG. 8 is a diagram for illustrating an example of recorded images displayed as a list according to the present embodiment.

As shown in FIG. 7, if recorded images 61, 62, 63 and 64 with gravity information are displayed as a list, in an image list 65 displayed on the display portion 102a, only the recorded images 61 to 64 are displayed and inspection information including gravity information is not displayed. For this reason, by merely viewing the recorded images 61 to 64 displayed in the image list 65, the user cannot recognize gravity information on the recorded images 61 to 64 displayed as a list.

Thus, as shown in FIG. 8, if the recorded images 61 to 64 with gravity information are displayed as a list, the main control portion 112 being a display control portion rotates the recorded images 61 to 64 in accordance with their gravity directions. Specifically, the main control portion 112 rotates the recorded images 61 to 64 so that the gravity directions of the recorded images 61 to 64 are downward as seen from the front of FIG. 8. It is assumed that the recorded images 61, 62, 63 and 64 rotated in this way are defined as recorded images 61a, 62a, 63a and 64a. Then, the main control portion 112 displays the rotated recorded images 61a to 64a as a list in the image list 65. Thus, since all the gravity directions of the recorded images 61a to 64a displayed as a list point downward, recognizability for the user is improved.

It should be noted that because the recorded images 61a to 64a displayed as a list in the image list 65 in FIG. 8 include slanting images, specifically, the recorded images 63a and 64a, a rotating process may be executed as follows.

Figure 9:
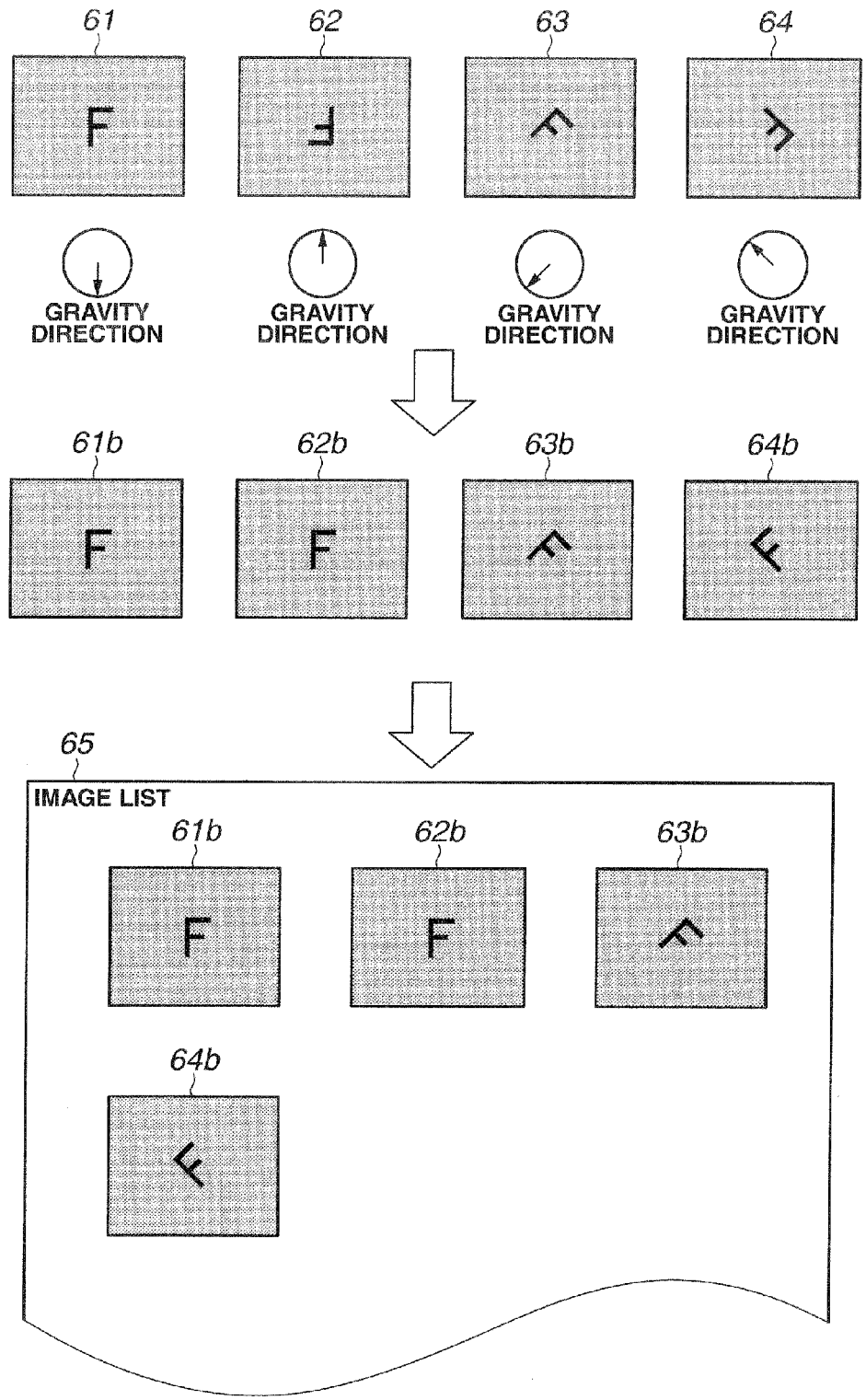
FIG. 9 is a diagram for illustrating another example of recorded images displayed as a list.
Figure 10:
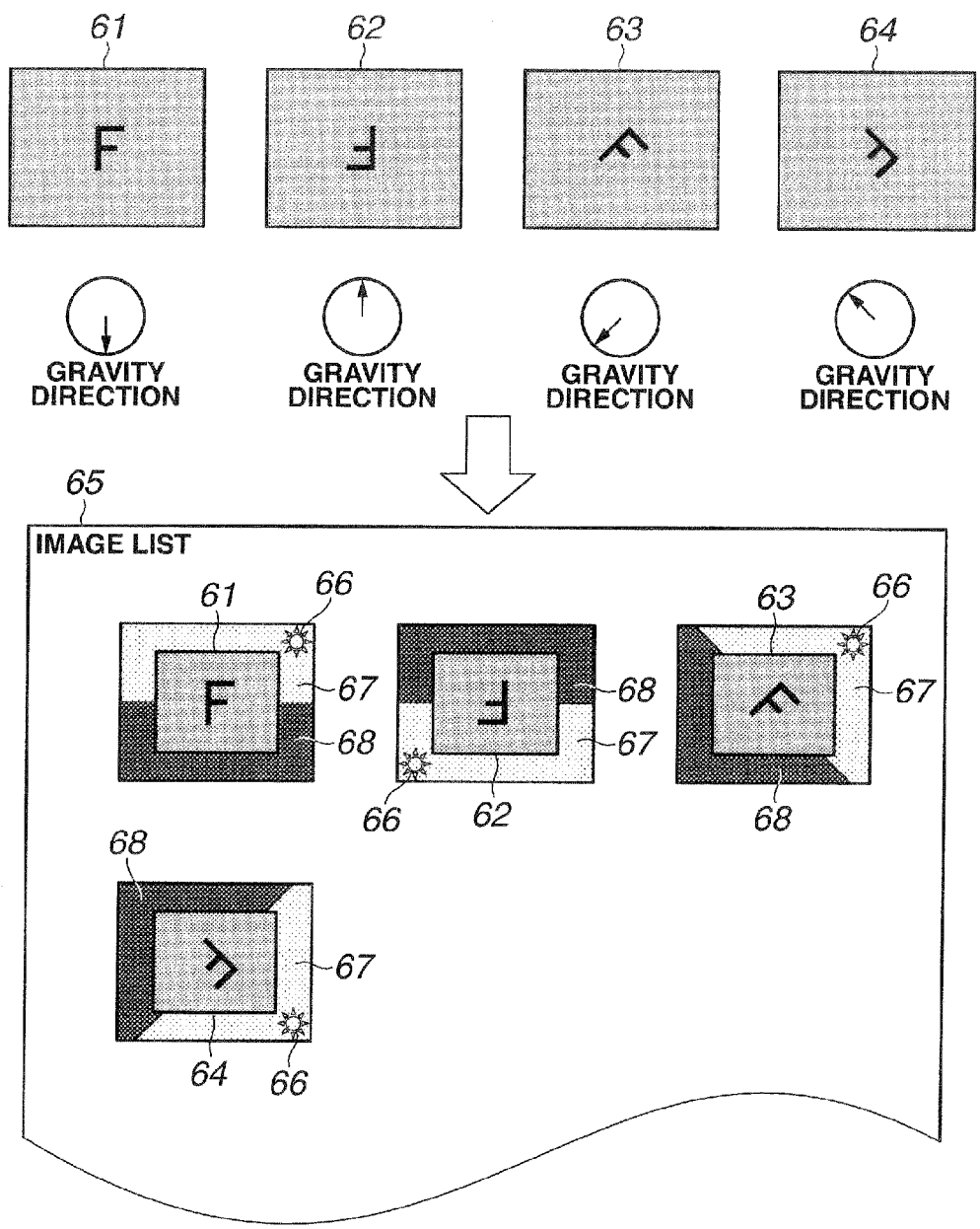
FIG. 10 is a diagram for illustrating still another example of recorded images displayed as a list.

FIG. 9 and FIG. 10 are diagrams for illustrating other examples of recorded images displayed as a list.

As shown in FIG. 9, only if the gravity directions of the recorded images 61 to 64 are upper half directions, the main control portion 112 rotates the recorded images 61 to 64 180 degrees. That is, since the gravity directions of the recorded images 61 and 63 are lower half directions, the recorded images 61 and 63 become unrotated recorded images 61b and 63b. On the other hand, since gravity information on the recorded images 62 and 64 indicates upper half directions, the recorded images 62 and 64 become recorded images 62b and 64b rotated 180 degrees. The main control portion 112 displays these recorded images 61b to 64b as a list in the image list 65.

Also, if the recorded images 61 to 64 are displayed as a list in the image list 65, the main control portion 112 may display indicators indicating gravity information in background of the recorded images 61 to 64.

As shown in FIG. 10, the main control portion 112 displays, in the background of each of recorded images 61 to 64, an indicator 66 composed of a predetermined mark and indicating a skyward direction, an indicator 67 indicating the skyward direction with a predetermined color, and an indicator 68 indicating a groundward direction with a color different from the predetermined color. Also, the main control portion 112 may display at least one of the indicators 66 to 68 in the background of the recorded images 61 to 64.

Next, a processing of displaying moving image frames in the AVI file 30 as a list will be described.

Figure 11:
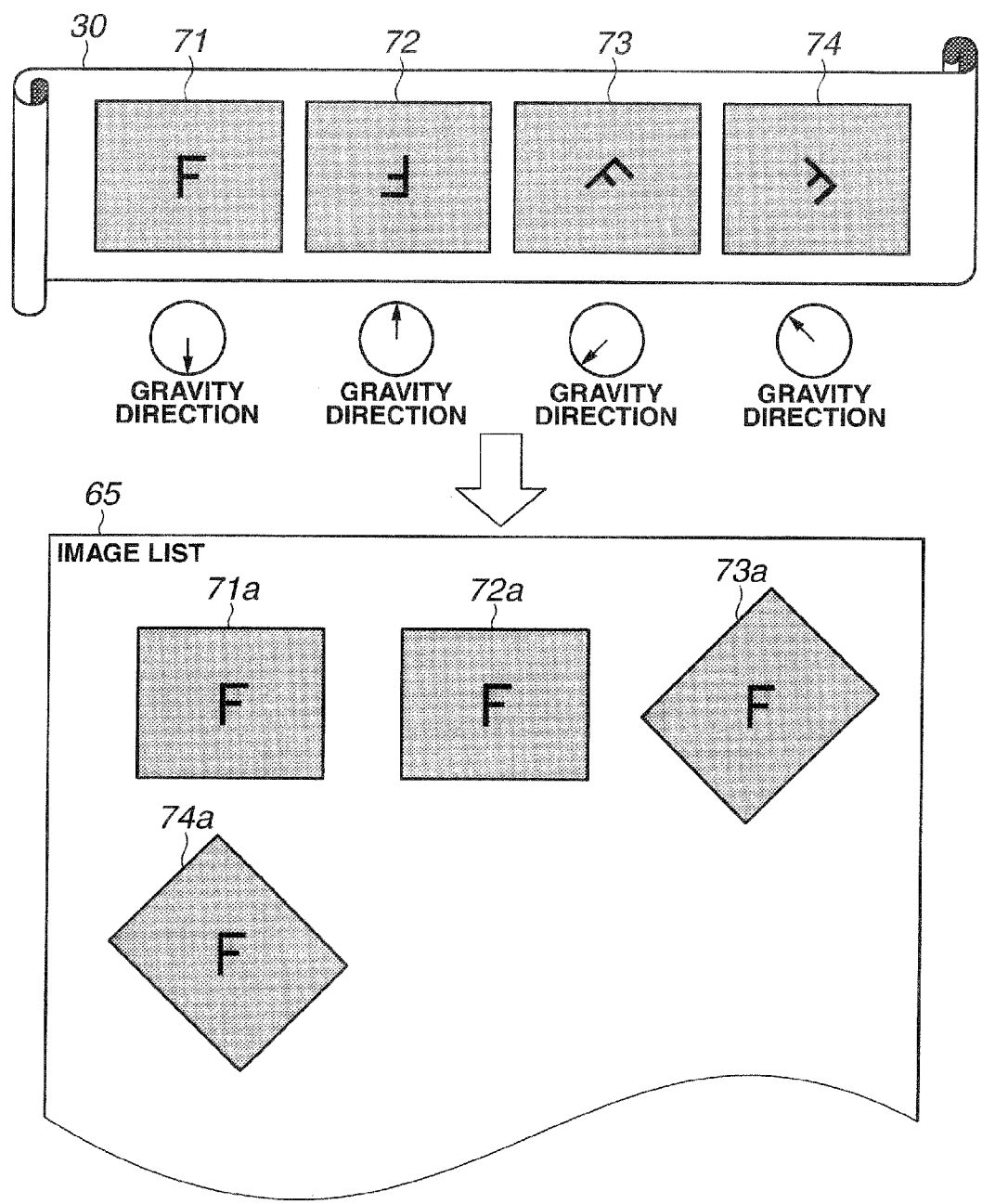
FIG. 11 is a diagram for illustrating an example of moving image frames displayed as a list.
Figure 12:
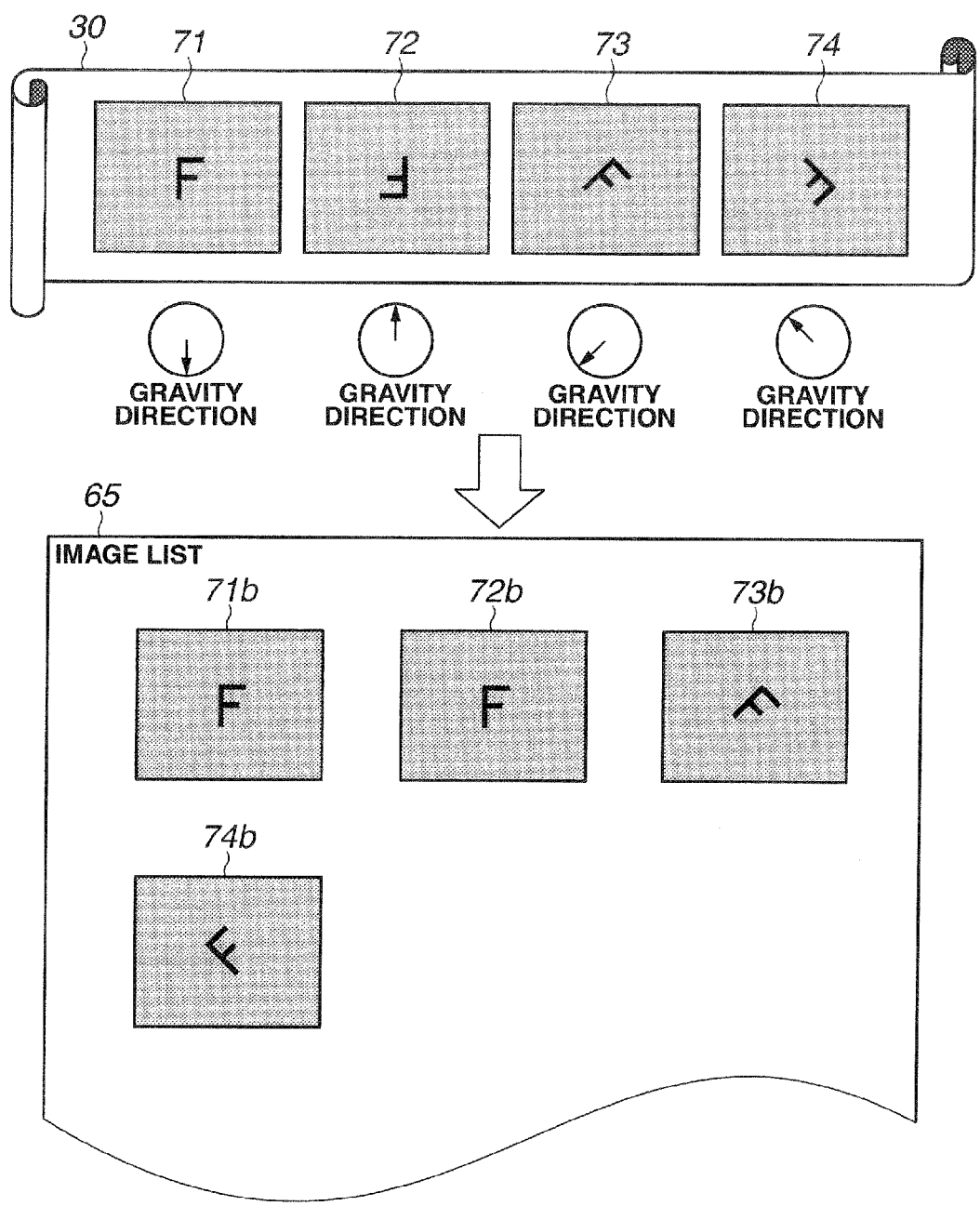
FIG. 12 is a diagram for illustrating another example of moving image frames displayed as a list.
Figure 13:
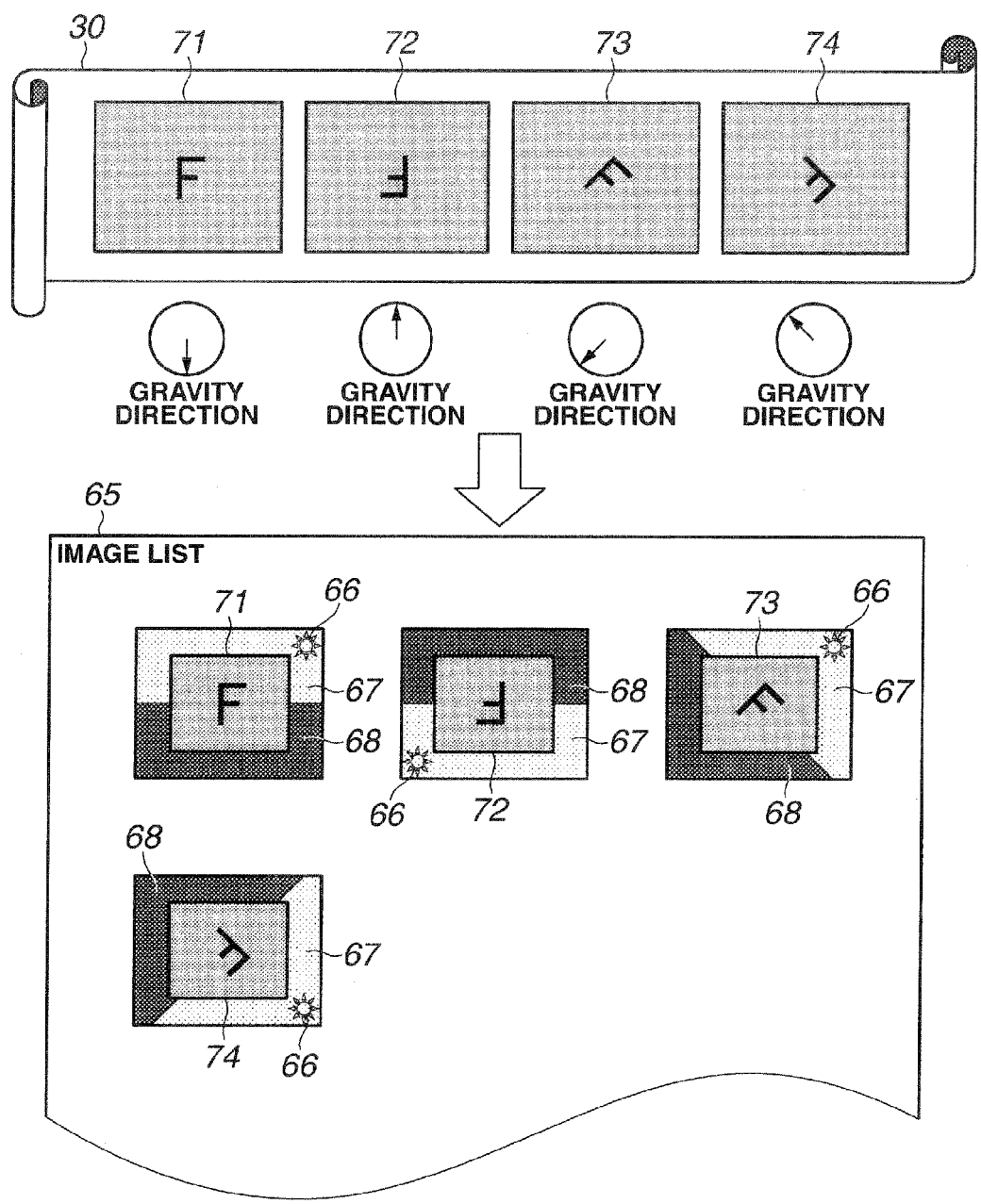
FIG. 13 is a diagram for illustrating still another example of moving image frames as a list.

FIG. 11 is a diagram for illustrating an example of moving image frames displayed as a list, and FIG. 12 and FIG. 13 are diagrams for illustrating other examples of moving image frames displayed as a list.

As shown in FIG. 11, moving image frames 71 to 74 in the AVI file 30 are each associated with gravity information as previously described. The main control portion 112 rotates the moving image frames 71 to 74 so that the gravity directions of the moving image frames 71 to 74 point downward in the same manner as the processing in FIG. 8. Then, the main control portion 112 displays rotated moving image frames 71a to 74a as a list in the image list 65.

Also, as shown in FIG. 12, only if the gravity directions of the moving image frames 71 to 74 are upper half directions, the main control portion 112 rotates the moving image frames 71 to 74 180 degrees. In an example shown in FIG. 12, the moving image frames 72 and 74 are rotated 180 degrees. Then, the main control portion 112 displays rotated moving image frames 71b to 74b as a list in the image list 65.

Also, as shown in FIG. 13, the main control portion 112 displays, in the background of each of the moving image frames 71 to 74, the indicator 66 composed of a predetermined mark and indicating the skyward direction, the indicator 67 indicating the skyward direction with a predetermined color, and the indicator 68 indicating the groundward direction with a color different from the predetermined color.

It should be noted that the moving image frames 71 to 74 displayed as a list in the image list 65 are not limited to the sequential moving image frames 71 to 74, and moving image frames to be displayed as a list may be extracted from the AVI file 30 in accordance with any one of the following conditions. For example, when moving image frames to be displayed as a list are extracted, one moving image frame is extracted every predetermined time (every 10 seconds), the moving image frames are extracted if the gravity directions are drastically changed, or the moving image frames are extracted based upon a trigger (a point the inspector has checked at the same time of image taking).

Now, moving image recording processing with the endoscope apparatus 1 will be described.

Figure 14:
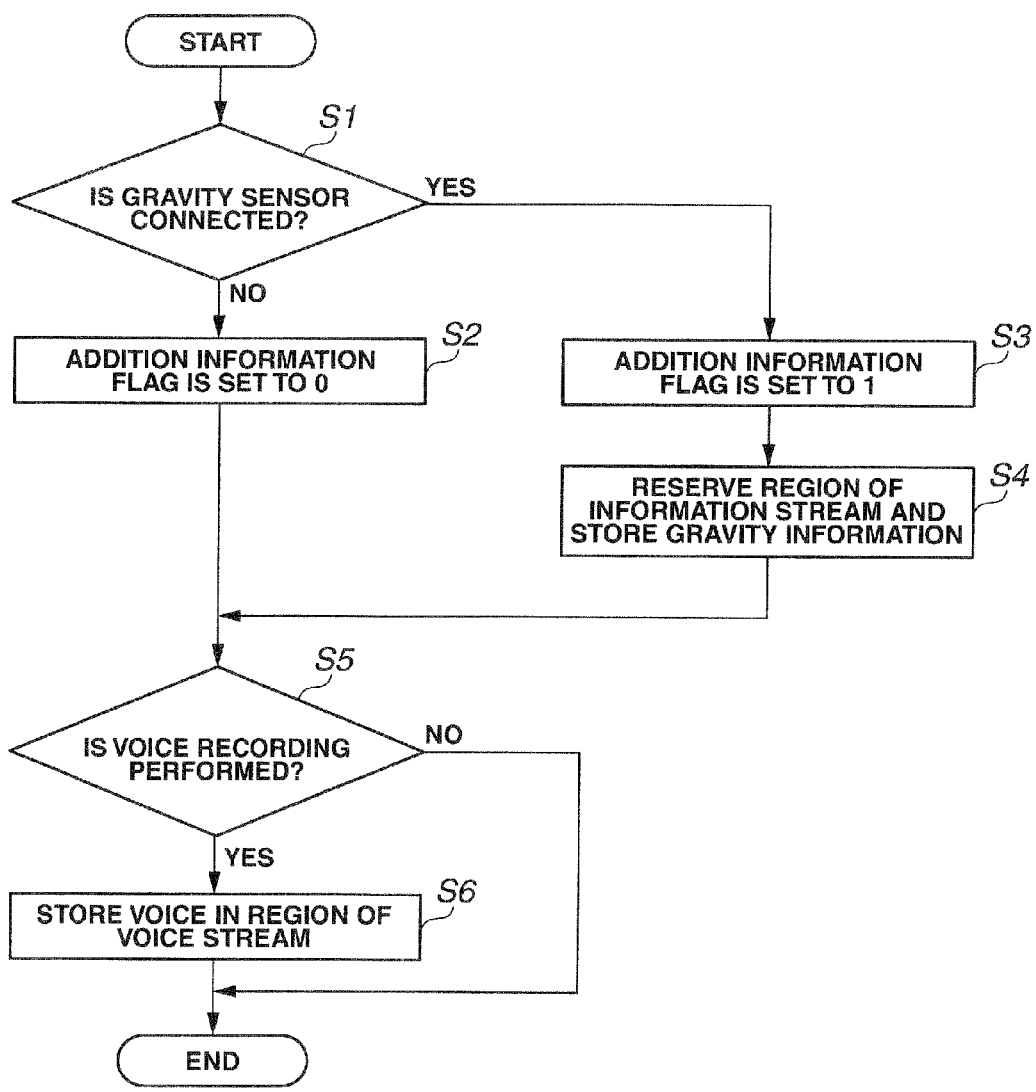
FIG. 14 is a flow chart for illustrating an example of a flow of moving image recording processing.

FIG. 14 is a flow chart for illustrating an example of a flow of the moving image recording processing.

First, if the inspector uses the operation portion 5 to instruct the endoscope apparatus 1 to perform the moving image recording processing, it is determined whether or not a gravity sensor, here, the gravity direction detecting portion 7 is connected (step S1). If it is determined that the gravity sensor is not connected (S1: No), an addition information flag is set to 0 (step S2). In contrast, if it is determined that the gravity sensor is connected (S1: Yes), the addition information flag is set to 1 (step S3). A region of an information stream is reserved and gravity information is stored therein (step S4). It should be noted that as previously described, if voice recording is not performed, gravity information may also be recorded in a region of a voice stream.

Next, if the process in step S2 or step S4 is executed, it is determined whether or not voice recording is performed (step S5). If it is determined that the voice recording is performed (step S5: Yes), then voice information is stored in a region of a voice stream (step S6), and the moving image recording processing is terminated. In contrast, if it is determined that the voice recording is not performed (step S5: No), then the moving image recording processing is terminated.

Next, moving image reproducing processing in which the reproducing apparatus 100 is used will be described.

Figure 15:
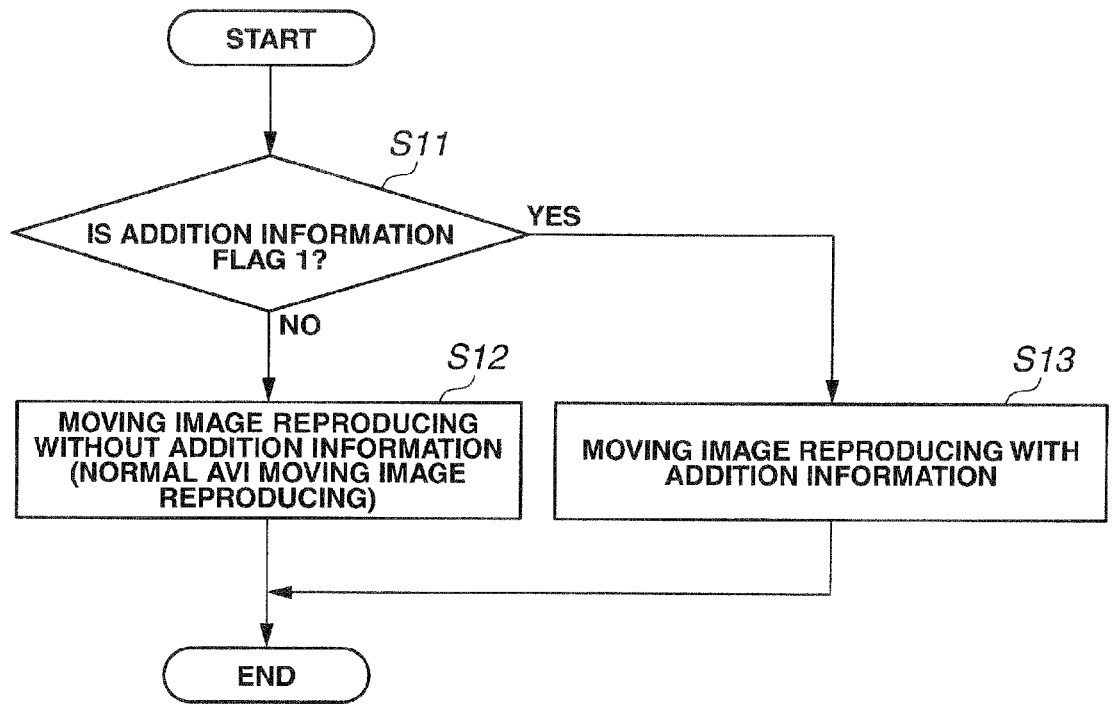
FIG. 15 is a flow chart for illustrating an example of a flow of moving image reproducing processing.

FIG. 15 is a flow chart for illustrating an example of a flow of the moving image reproducing processing.

First, if the inspector uses the operation portion 103 to instruct the reproducing apparatus 100 to perform the moving image reproducing processing, the AVI file 30 is retrieved from the recording medium 17, and it is determined whether or not an addition information flag in the AVI file 30 is 1 (step S11). If it is determined that the addition information flag is not 1 (step S11: No), moving image reproducing without addition information is performed (step S12), and the processing of the moving image reproducing is terminated. In contrast, if it is determined that the addition information flag is 1 (step S11: Yes), moving image reproducing with addition information is performed (step S13), moving image reproducing the processing is terminated. In the moving image reproducing with addition information, shown in step S13, for example, the indicator 22a indicating the gravity direction shown in FIG. 3A is generated, combined to an endoscope image, and then displayed on the display portion 102a.

As hereinbefore described, the endoscope apparatus 1 adds a region of the information stream 43a in the stream data portion 33 of the AVI file 30 and stores gravity information detected by the gravity direction detecting portion 7 in the region of the information stream 43a. As a result, when the inspector uses the reproducing apparatus 100 to perform a detailed inspection, the gravity direction is displayed with a moving image.

Thus, according to the endoscope apparatus of the present embodiment, a moving image file for a detailed inspection can be easily generated.

Also, since information about the gravity direction can be obtained from a recorded moving image file, for example, at the time of the moving image reproducing processing, an endoscope image can be reproduced at any angle by rotating the image so that the gravity direction is always downward.

Second Embodiment

Next, a second embodiment will be described.

When the inspector performs a detailed inspection using the AVI file 30 of the first embodiment, if a flaw is found in an object, the inspector may inspect the object again. In this case, with only gravity direction information, the inspector has no idea of how deep the insertion portion 2 is inserted in the object, so that when the inspection is performed again, the insertion portion 2 may not reach again the same place, where the flaw has been found.

Thus, in the present embodiment, an endoscope apparatus will be described which records gravity direction information as well as insertion length information about the insertion portion 2 on the AVI file 30.

Figure 16:
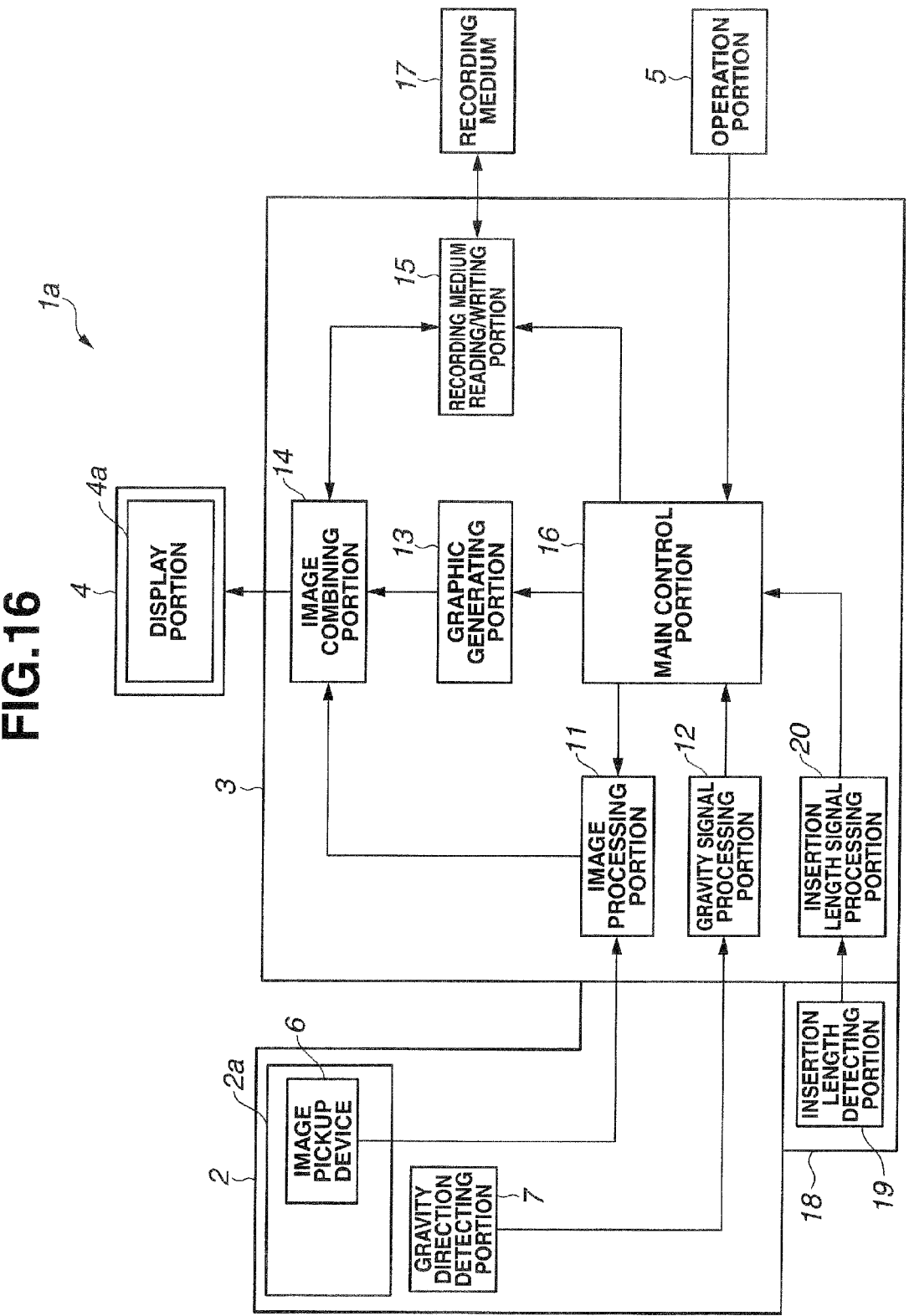
FIG. 16 is a block diagram showing an entire configuration of an endoscope apparatus according to a second embodiment.

FIG. 16 is a block diagram showing an entire configuration of an endoscope apparatus according to the second embodiment. In FIG. 16, the same reference numerals are assigned to the same components as those in FIG. 2, and a description thereof is omitted.

As shown in FIG. 16, in an endoscope apparatus 1a, a root portion 18 including an insertion length detecting portion 19 is added to a root of the insertion portion 2 of the endoscope apparatus 1 in FIG. 2, and an insertion length signal processing portion 20 is added in the main body portion 3.

The insertion length detecting portion 19 detects information about an insertion length of the distal end portion 2a and outputs a signal of the detected information about the insertion length of the distal end portion 2a to the insertion length signal processing portion 20.

If the insertion length signal processing portion 20 receives the information signal about the insertion length of the distal end portion 2a outputted from the insertion length detecting portion 19 (as input), the insertion length signal processing portion 20 converts the information signal into insertion length information on a distance between the distal end portion 2a and the main body portion 3 and supplies the converted insertion length information to the main control portion 16.

If the graphic generating portion 13 receives the insertion length information from the main control portion 16 (as input), the graphic generating portion 13 generates an indicator indicating the insertion length and supplies the generated indicator indicating the insertion length to the image combining portion 14. Further, the graphic generating portion 13 supplies the image combining portion 14 with the indicator indicating the gravity direction as described in the first embodiment.

The image combining portion 14 combines an endoscope image supplied from the image processing portion 11 with the indicator indicating the gravity direction and the insertion length, supplied from the graphic generating portion 13, into one sheet of video data, and outputs the combined image to the display device 4. As a result, the combined image is displayed on the display portion 4a of the display device 4.

Also, in response to the control of the main control portion 16, the image combining portion 14 may display an endoscope image solely on the display portion 4a of the display device 4, or may display an endoscope image and an indicator indicating an insertion length.

FIGS. 17A to 17C are diagrams showing examples of a display screen on which gravity information and insertion length information are displayed. In FIG. 17A to FIG. 17C, the same reference numerals are assigned to the same elements as those in FIGS. 3A to 3C, and a description thereof is omitted.

As shown in FIG. 17A, if an insertion length detected by the insertion length detecting portion 19 is "aaaaa," then the graphic generating portion 13 generates an indicator 23a indicating the insertion length. Then, the image combining portion 14 combines the indicator 23a on a lower right side of an endoscope image, and the indicator 23a is displayed on the display portion 4a of the display device 4.

In the same manner, as shown in FIG. 17B, if an insertion length detected by the insertion length detecting portion 19 is "bbbbb," then the graphic generating portion 13 generates an indicator 23b indicating the insertion length. Then, the image combining portion 14 combines the indicator 23b on a lower right side of an endoscope image, and the indicator 23b is displayed on the display portion 4a of the display device 4.

Further, as shown in FIG. 17C, if an insertion length detected by the insertion length detecting portion 19 is "ccccc," then the graphic generating portion 13 generates an indicator 23c indicating the insertion length. Then, the image combining portion 14 combines the indicator 23c on a lower right side of an endoscope image, and the indicator 23c is displayed on the display portion 4a of the display device 4.

In accordance with control of the main control portion 112, the recording medium reading/writing portion 111 provides the stream data 33a of the AVI file 30 shown in FIG. 4 with a region of an information stream similar to the region of the information stream 43a and stores insertion length information data indicating an insertion length in the information stream region. As a result, the display portion 102a of the reproducing apparatus 100 displays an endoscope image with which the gravity information and the insertion length information as shown in FIG. 17A to FIG. 17C are displayed.

Figure 18A:
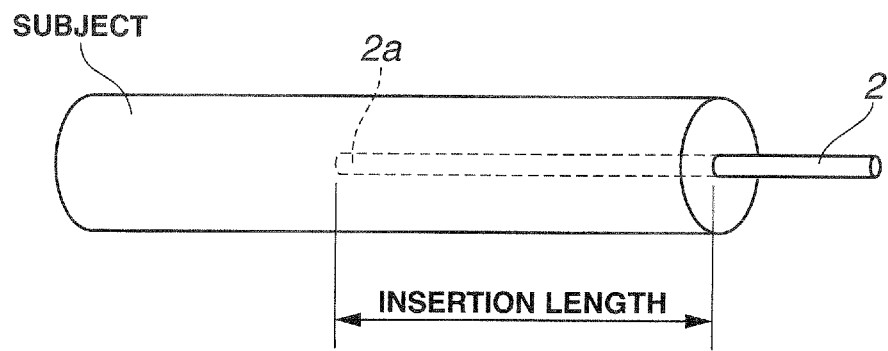
FIGS. 18A and 18B are diagrams for illustrating a relationship between gravity directions and insertion lengths of a distal end portion.
Figure 18B:
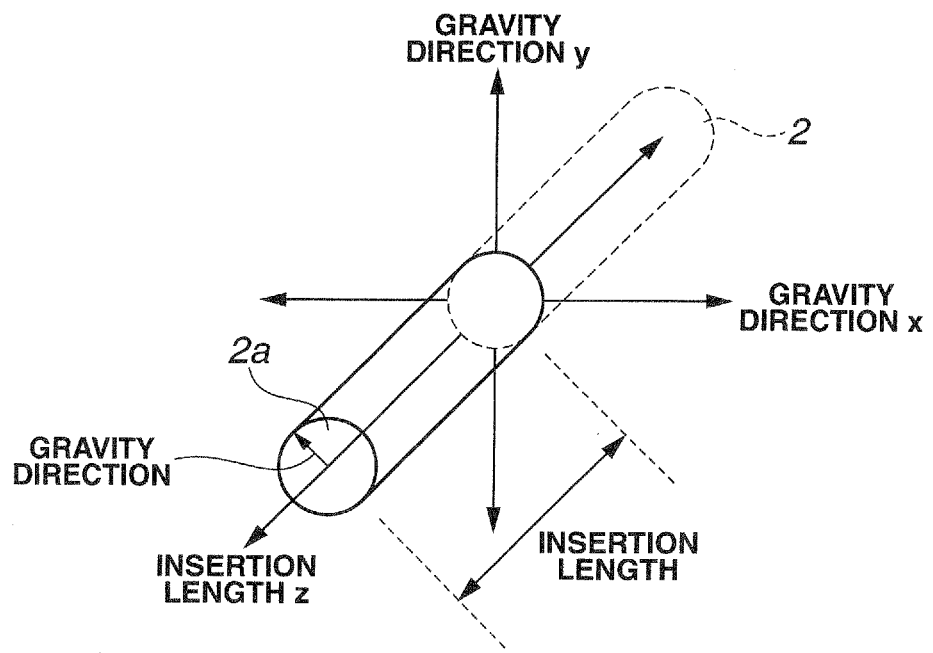

FIGS. 18A and 18B are diagrams for illustrating a relationship between gravity directions and insertion lengths of the distal end portion.

The inspector may inspect a pipe as an object. Because pipe corrosion often occurs at a lower side of a pipe, the inspector uses a side-view type endoscope apparatus to obtain an endoscope image at a lower side of a pipe. However, if the long-length insertion portion 2 is inserted into such an object, the distal end portion 2a of the insertion portion 2 may rotate and disadvantageously an image of an upper side of the pipe may be taken.

In the present embodiment, information about a gravity direction and an insertion length of the distal end portion 2a of the insertion portion 2 can be obtained from the AVI file 30. That is, as shown in FIGS. 18A and 18B, gravity direction information on the distal end portion 2a of the insertion portion 2 in a two-dimensional plane composed of gravity directions x and y, and insertion length information on the distal end portion 2a of the insertion portion 2 in an insertion length z direction can be obtained. The information about the gravity direction and the insertion length can be used as three-dimensional coordinates information for identifying at which position in the object the endoscope image has been taken. Then, by combining endoscope images identified using the three-dimensional coordinates information, a three-dimensional structure of the object can be mapped.

Accordingly, the inspector can recognize at which position in an object an inspection omission occurs; for example, a side-view type endoscope apparatus takes an image of an upper side of a pipe by mistake. As a result, when an inspection is performed again, the inspector can more accurately and easily allow the distal end portion 2a of the insertion portion 2 to reach a desired position by using the endoscope apparatus 1a to obtain the gravity direction and the insertion length information on the distal end portion 2a.

Third Embodiment

Next, a third embodiment will be described. In the third embodiment, an inspection report generating apparatus for generating the inspection report shown in FIG. 6 will be described.

Figure 19:
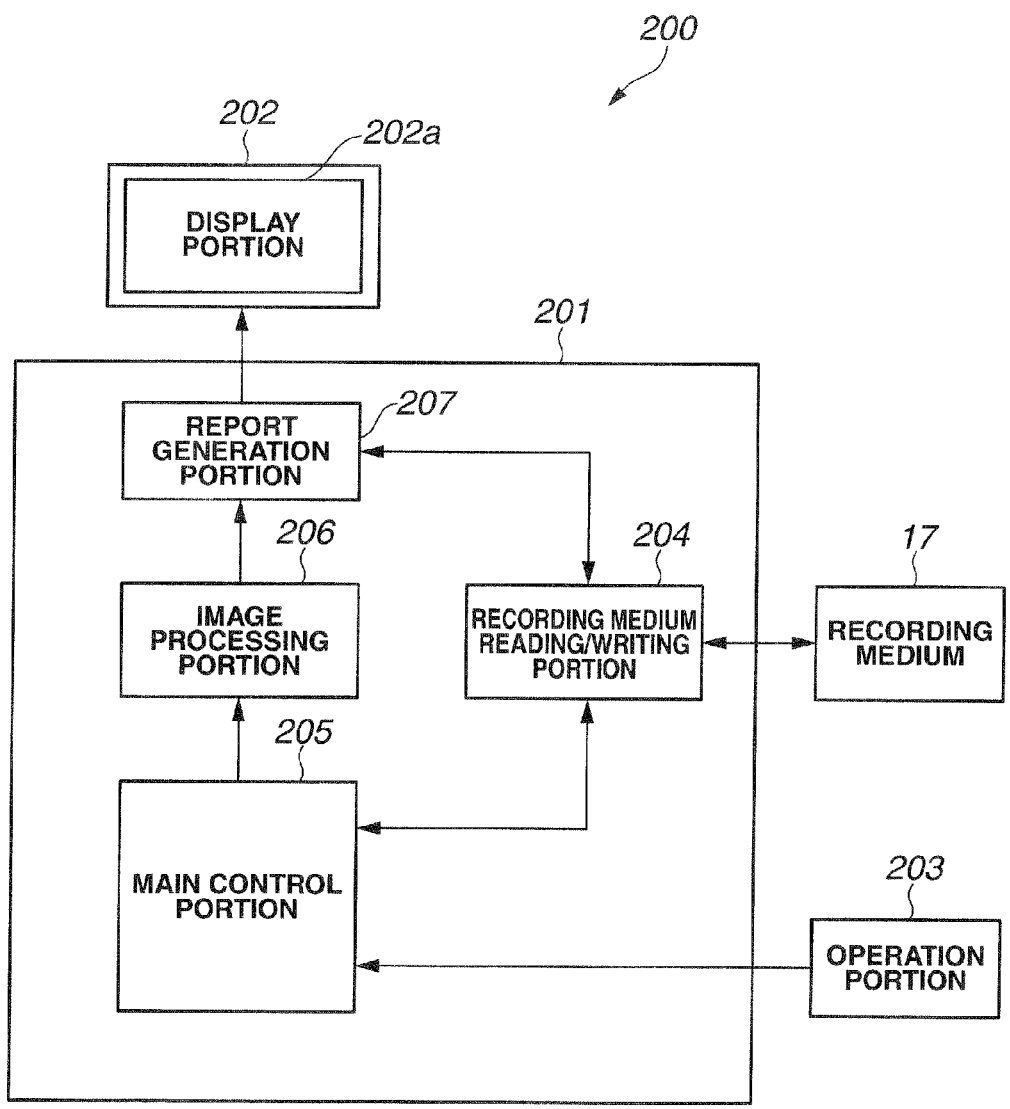
FIG. 19 is a block diagram showing an example of a configuration of an inspection report generating apparatus for generating an inspection report.

FIG. 19 is a block diagram showing an example of a configuration of the inspection report generating apparatus for generating the inspection report.

An inspection report generating apparatus 200. e.g., a personal computer, includes a main body portion 201, a display device 202 having a display portion 202a such as an LCD, and an operation portion 203 for performing various operations, such as a keyboard or a mouse.

The main body portion 201 includes a recording medium reading/writing portion 204, a main control portion 205, an image processing portion 206, and a report generating portion 207.

The recording medium 17 is detachably connected to the main body portion 201. In the recording medium 17, a recorded image (a still image) and the AVI file 30 (a moving image file) are recorded, as well as an inspection report template shown in FIG. 20 is recorded.

Figure 20:
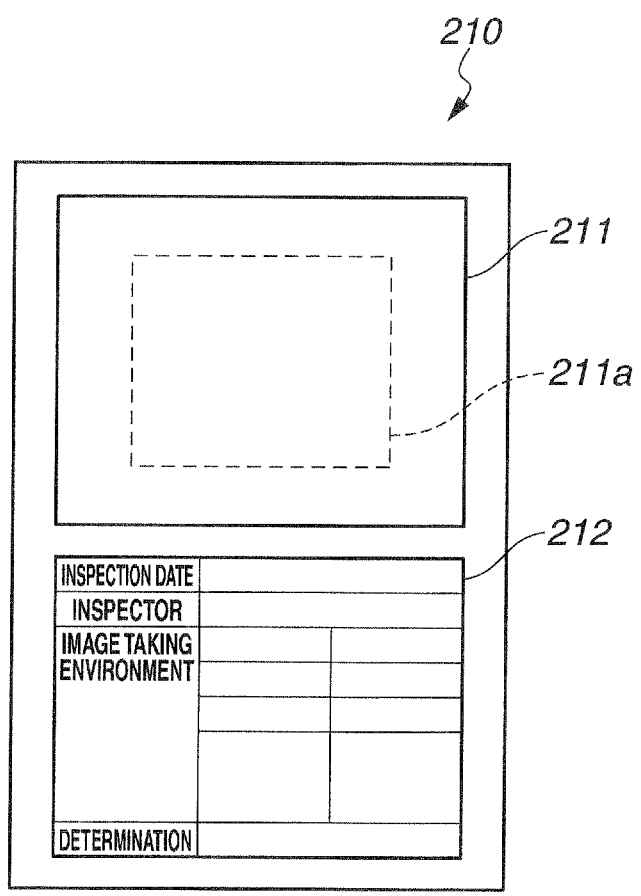
FIG. 20 is a diagram for illustrating an example of an inspection report template.

FIG. 20 is a diagram for illustrating an example of the inspection report template.

As shown in FIG. 20, an inspection report template 210 includes an image recording area 211 in which an image recorded as a still image and an inspection image such as moving image frames in the AVI file 30 are pasted and an inspection condition input area 212 in which inspection conditions are inputted. More specifically, an inspection image is pasted in a predetermined region 211a of the image recording area 211. Also, as described later, an inspection image may be rotated based on gravity information so that the gravity direction becomes downward before the image is pasted in the image recording area 211. Further, as shown in FIG. 6, for example, an inspection image may be fitted to the image recording area 211 and then pasted therein.

The recording medium reading/writing portion 204 retrieves the inspection report template 210 recorded on the recording medium 17 and outputs the template 210 to the report generating portion 207. Also, the recording medium reading/writing portion 204 retrieves a recorded image and the AVI file 30 recorded on the recording medium 17 and outputs the retrieved recorded image and AVI file 30 to the main control portion 205.

The main control portion 205 selects an inspection image for creating a report from the retrieved recorded image and AVI file 30 and outputs the selected inspection image and gravity information thereof to the image processing portion 206. Such an inspection image is selected by, for example, the inspector operating the operation portion 203.

The image processing portion 206 rotates the inspection image based on the inputted gravity information so that the gravity direction of the inspection image becomes downward and outputs the rotated inspection image to the report generating portion 207.

Now, a rotating process of the image processing portion 206 will be described.

Figure 21:
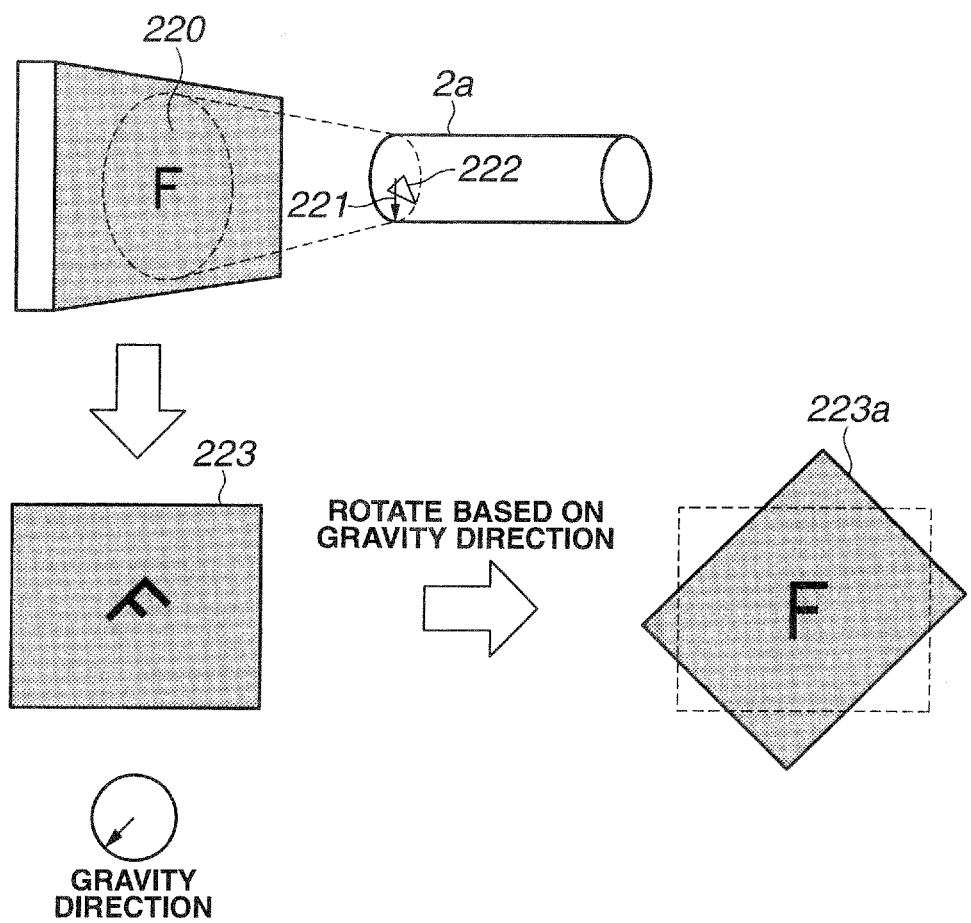
FIG. 21 is a diagram for illustrating an inspection image rotating process.

FIG. 21 is a diagram for illustrating the inspection image rotating process.

As shown in FIG. 21, when the distal end portion 2a of the insertion portion 2 is used to pick up an image of an object 220, if a gravity downward direction (an arrow 221 in the figure) does not match a downward direction (a triangle 222) of the distal end portion 2a (on the image pickup screen), since the gravity direction of an inspection image 223 is not downward, recognizability is low.

Thus, the image processing portion 206 rotates the inspection image 223 based on gravity information on the inspection image 223 so that the gravity direction of the inspection image 223 points down, and thereby a rotated inspection image 223a is obtained. The rotated inspection image 223a is outputted to the report generating portion 207. If the image processing portion 206 determines that the rotated inspection image 223a does not fit into the image recording area 211, the image processing portion 206 reduces the inspection image 223a so as to fit into the image recording area 211 and then outputs the reduced image to the report generating portion 207.

The report generating portion 207 combines the rotated inspection image 223a in the inspection report template 210 retrieved by the recording medium reading/writing portion 204 to generate an inspection report. The generated inspection report is displayed on the display portion 202a or recorded on the recording medium 17 through the recording medium reading/writing portion 204.

Figure 22:
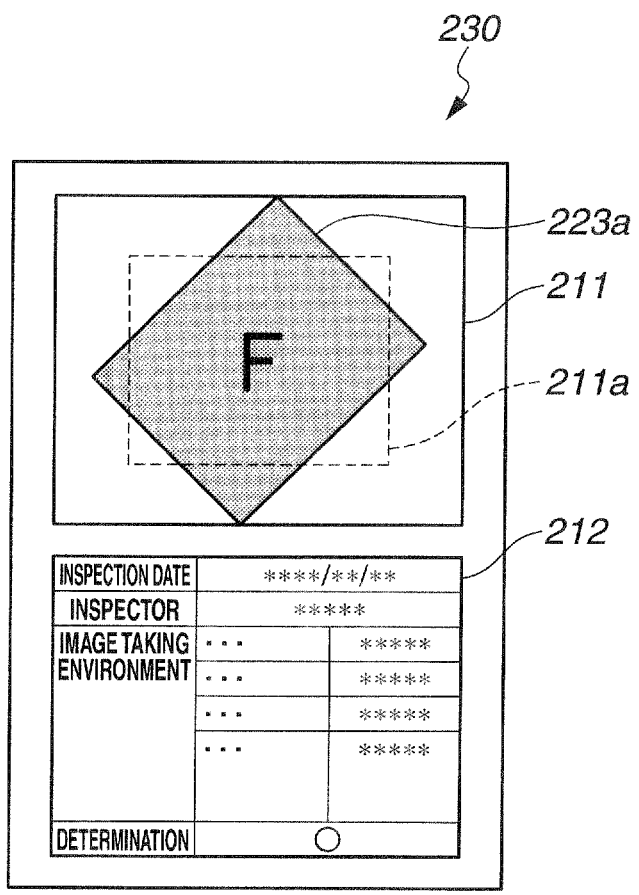
FIG. 22 is a diagram for illustrating an example of an inspection report on which an inspection image is pasted.

The inspection report generated in this manner is shown in FIG. 22.

FIG. 22 is a diagram for illustrating an example of an inspection report on which an inspection image is pasted.

As shown in FIG. 22, in the image recording area 211 of an inspection report 230, the inspection image 223a rotated from the predetermined region 211a so that the gravity direction becomes downward is pasted. Also, in the inspection condition input area 212 of the inspection report 230, inspection conditions are inputted through the operation portion 203.

It should be noted that in the example of FIG. 22, although the inspection image 223a with the gravity direction always pointing downward is pasted in the image recording area 211, the slanting inspection image 223a is pasted in the image recording area 211. Thus, the image processing portion 206 rotates the inspection image 223 so that the gravity direction thereof points down as well as if the gravity direction of the inspection image 223 is one of upper half directions, the image processing portion 206 rotates the inspection image 223 180 degrees.

FIG. 23 to FIG. 26 are diagrams for illustrating other examples of the inspection image rotating process.

Figure 23:
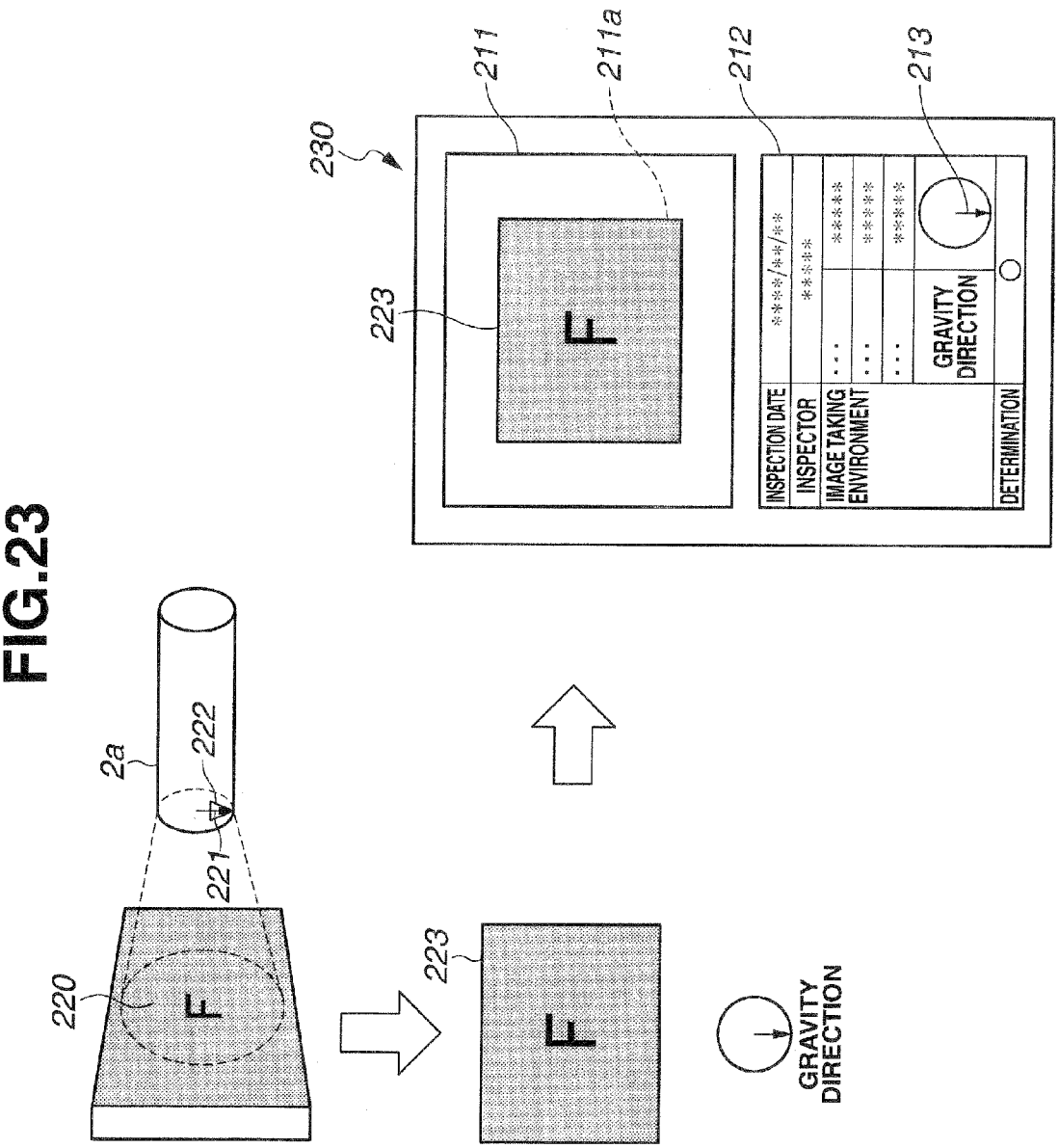
FIG. 23 is a diagram for illustrating another example of the inspection image rotating process.

As shown in FIG. 23, if a downward direction of the distal end portion 2a of the insertion portion 2 (the triangle 222) points downward, the gravity direction of the inspection image 223 is one of lower half directions. In this case, the image processing portion 206 outputs the inspection image 223 to the report generating portion 207 without rotating the image 223. The report generating portion 207 combines the unrotated inspection image 223a in the predetermined region 211a of the image recording area 211 of the template 210.

Figure 25:
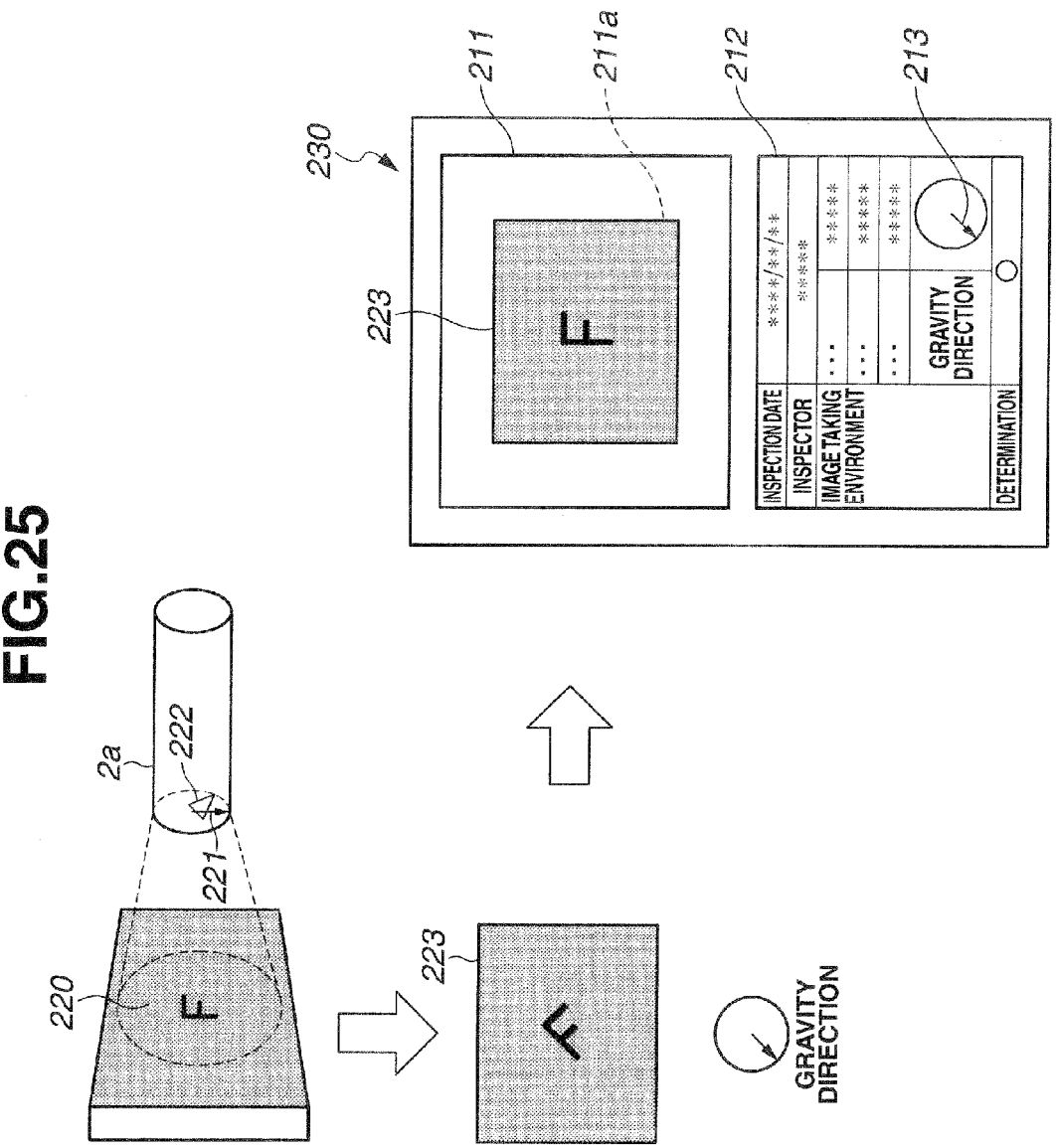
FIG. 25 is a diagram for illustrating yet another example of the inspection image rotating process.
Figure 26:
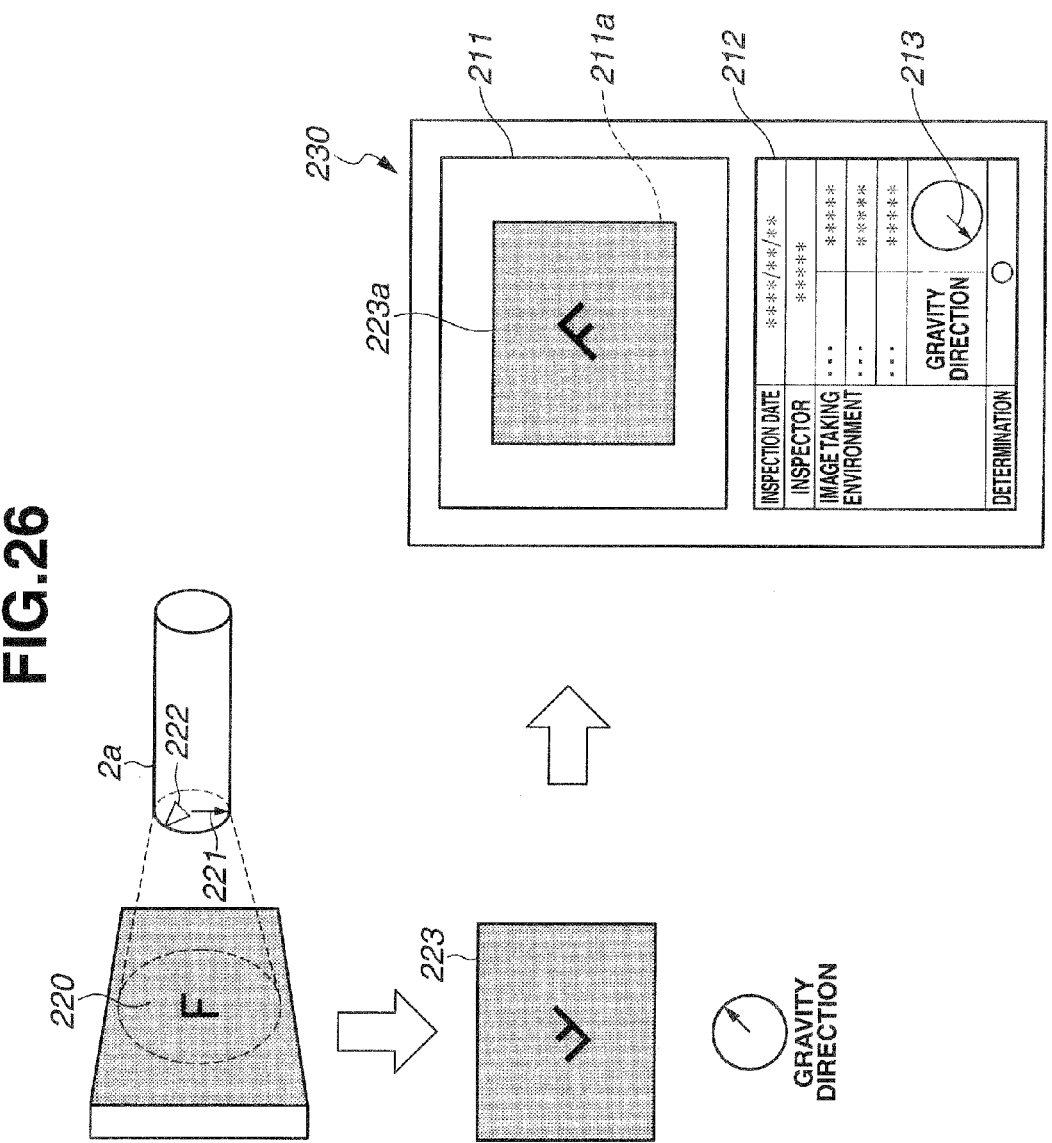
FIG. 26 is a diagram for illustrating yet another example of the inspection image rotating process.

In the inspection report 230 generated in this way, an arrow 213 indicating the gravity direction is written in an item of image taking environment of the inspection condition input area 212. As shown in FIG. 25 and FIG. 26 described later, because the gravity direction of the combined inspection image 223a is not downward depending on image taking conditions, information indicating the gravity direction is written.

Also, as shown in FIG. 24, if a downward direction of the distal end portion of the insertion portion 2 (the triangle 222) points upward, the gravity direction of the inspection image 223 is one of upper half directions. In this case, the image processing portion 206 rotates the inspection image 223 180 degrees and outputs the rotated inspection image 223a to the report generating portion 207. The report generating portion 207 combines the rotated inspection image 223a in the predetermined region 211a of the image recording area 211 of the template 210.

Also, as shown in FIG. 25, if a downward direction of the distal end portion 2a of the insertion portion 2 (the triangle 222) points obliquely downward, the gravity direction of the inspection image 223 is one of lower half directions. In this case, the image processing portion 206 outputs the inspection image 223 to the report generating portion 207 without rotating the image 223. The report generating portion 207 combines the unrotated inspection image 223a in the predetermined region 211a of the image recording area 211 of the template 210.

Also, as shown in FIG. 26, a downward direction of the distal end portion 2a of the insertion portion 2 (the triangle 222) points obliquely upward, the gravity direction of the inspection image 223 is one of upper half directions. In this case, the image processing portion 206 rotates the inspection image 223 180 degrees and outputs the rotated inspection image 223a to the report generating portion 207. The report generating portion 207 combines the rotated inspection image 223a in the predetermined region 211a of the image recording area 211 of the template 210.

In this manner, if the gravity direction of the inspection image 223 is lower half directions, the image processing portion 206 does not rotate the inspection image 223. If the gravity direction of the inspection image 223 is upper half directions, the image processing portion 206 rotates the inspection image 223 180 degrees. As a result, the slanting inspection image 223a is not pasted in the inspection report 230, and the gravity direction of the pasted inspection image 223a is always lower half directions, so that recognizability is improved.

Also, the image processing portion 206 may generate an indicator indicating skyward or groundward direction (the gravity direction) in a background of the inspection image 223.

Figure 27:
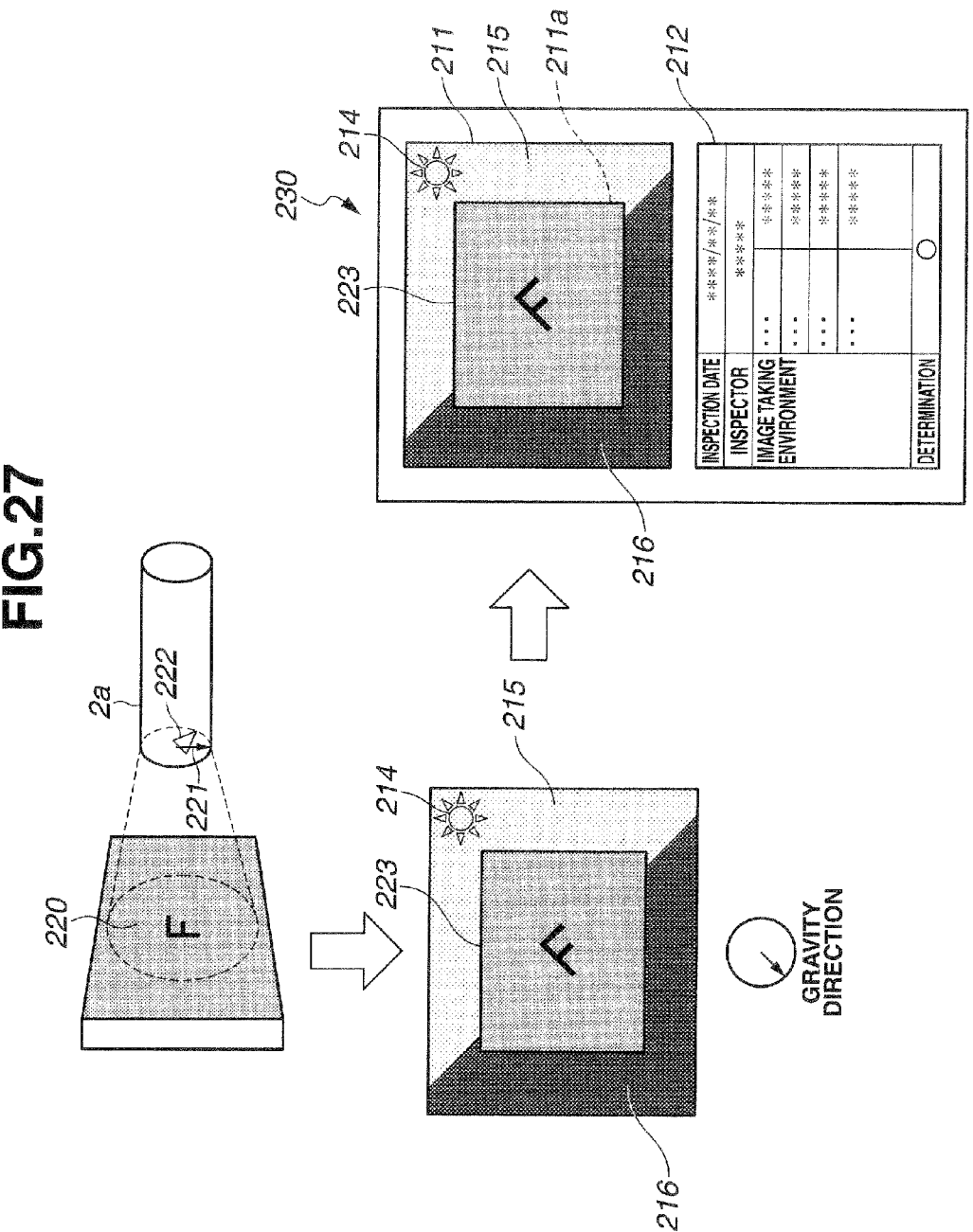
FIG. 27 is a diagram for illustrating an example of an indicator generating process.
Figure 28:
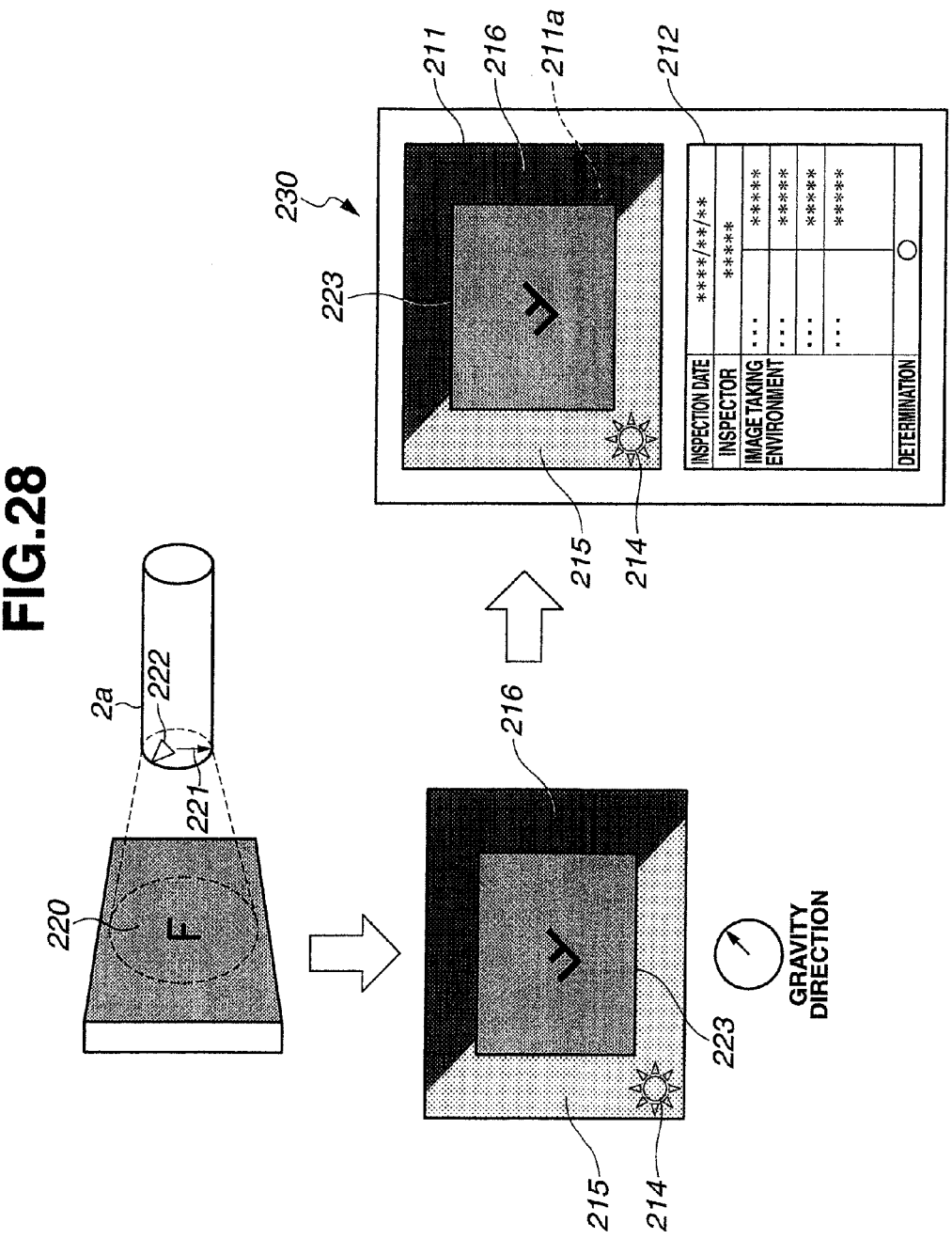
FIG. 28 is a diagram for illustrating an example of the indicator generating process.

FIG. 27 and FIG. 28 are diagrams for illustrating an example of the indicator generating process.

As shown in FIG. 27, based on the gravity direction of the inspection image 223, the image processing portion 206 generates an indicator 214 indicating the skyward direction composed of a predetermined mark, an indicator 215 indicating the skyward direction with a predetermined color, and an indicator 216 indicating the groundward direction with a color different from the predetermined color, in the background of the inspection image 223. For example, if the gravity direction of the inspection image 223 is obliquely downward to the left, the image processing portion 206 generates, in an obliquely upward direction to the right, the indicators 214 and 215 indicating the skyward direction and generates, in an obliquely groundward direction to the left, the indicator 216 indicating the groundward direction.

Also, as shown in FIG. 28, if the gravity direction of the inspection image 223 is obliquely upward to the right, the image processing portion 206 generates, in an obliquely downward direction to the left, the indicators 214 and 215 indicating the skyward direction and generates, in an obliquely skyward direction to the right, the indicator 216 indicating the groundward direction. The inspection image 223 and the indicators 214 to 216 generated in this manner are outputted to the report generating portion 207.

The report generating portion 207 combines (pastes) the inspection image 223 and the indicators 214 to 216 outputted from the image processing portion 206 in the image recording area 211 to generate the inspection report 230.

Next, an operation of the inspection report generating apparatus 200 having such a configuration will be described.

Figure 29:
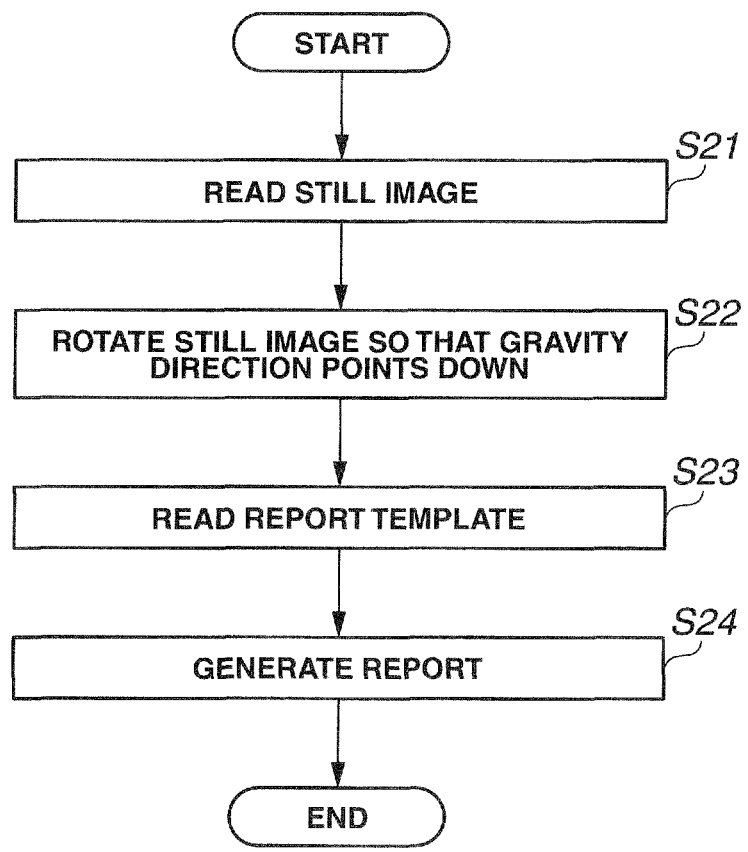
FIG. 29 is a flow chart for illustrating a flow example of a report generating process executed by an inspection report generating apparatus 200.

FIG. 29 is a flow chart for illustrating a flow example of a report generating process executed by the inspection report generating apparatus 200.

First, a still image recorded on the recording medium 17 is read (step S21). The still image is the above-mentioned inspection image 223. The image is not limited to a still image and may be, for example, a moving image frame in the AVI file 30. Next, the inspection image 223 is rotated so that the gravity direction of the read still image points downward (step S22). Next, the inspection report template 210 is read from the recording medium 17 (step S23). Finally, the inspection report 230 is generated (step S24), and the processing is terminated.

Figure 30:
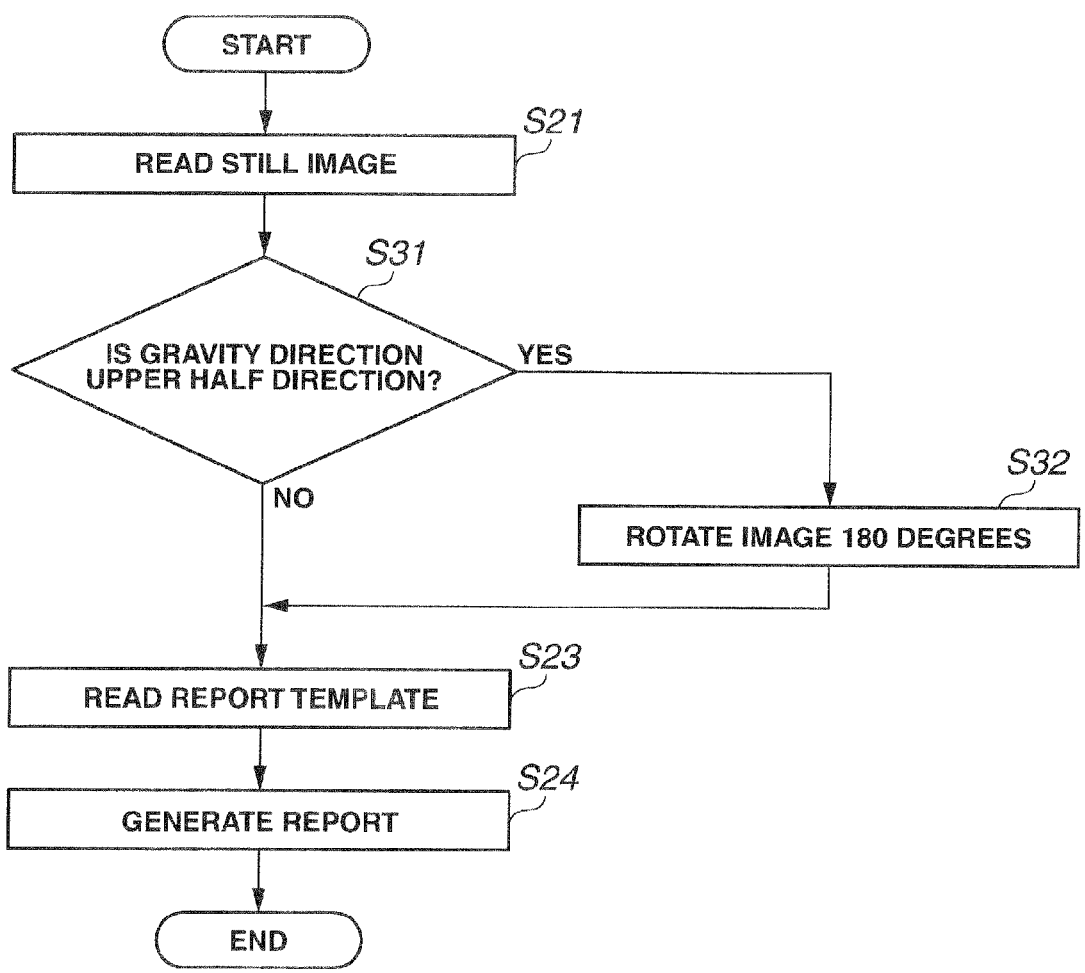
FIG. 30 is a flow chart for illustrating another flow example of the report generating process executed by the inspection report generating apparatus 200.

FIG. 30 is a flow chart for illustrating another flow example of the report generating process executed by the inspection report generating apparatus 200. It should be noted that in FIG. 30, the same reference numerals are assigned to the same processes as those in FIG. 29, and a description thereof is omitted.

First, if a still image is read in step S21, it is determined whether or not the gravity direction of the read still image is an upper half direction (step S31). If it is determined that the gravity direction of the still image is an upper half direction (step S31: Yes), the still image is rotated 180 degrees, and the processing proceeds to step S23. In contrast, if it is determined that the gravity direction of the still image is not an upper half direction (step S31: No), the still image is not rotated and the processing proceeds to step S23. Then, in step S23, the inspection report the template 210 is read from the recording medium 17, and in step S24, the inspection report 230 is generated. It should be noted that in the process in step S24, the still image read in step S21 or the still image rotated 180 degrees in step S32 is combined (pasted) in the predetermined region 211a of the image recording area 211 of the template 210.

Figure 31:
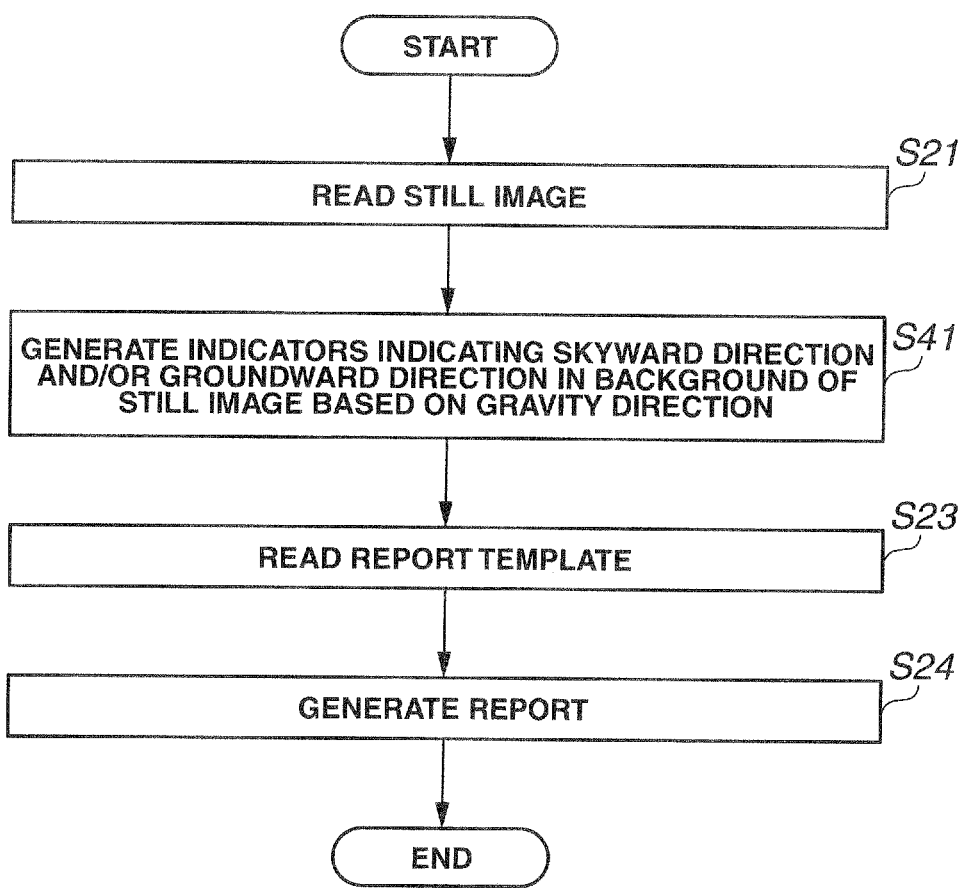
FIG. 31 is a flow chart for illustrating still another flow example of the report generating process executed by the inspection report generating apparatus 200.

FIG. 31 is a flow chart for illustrating still another flow example of the report generating process executed by the inspection report generating apparatus 200. It should be noted that in FIG. 31, the same reference numerals are assigned to the same processes in FIG. 29, and a description thereof is omitted.

First, if a still image is read in step S21, the indicators 214 and 215 indicating the skyward direction and/or the indicator 216 indicating the groundward direction are generated in the background of the still image based on the gravity direction (step S41). Then, in step S23, the inspection report template 210 is read from the recording medium 17, and in step S24, the inspection report 230 is generated. In the process in step S24, the still image and the indicators 214 to 216 are combined in the image recording area 211 of the template 210.

As hereinbefore described, the inspection report generating apparatus 200 rotates the inspection image 223 based on the gravity direction of the inspection image 223 so that the gravity direction points downward. Also, if the gravity direction of the inspection image 223 is an upper half direction, the inspection report generating apparatus 200 rotates the inspection image 180 degrees. Alternatively, the inspection report generating apparatus 200 generates the indicators 214 to 216 indicating the skyward direction and the groundward direction in the background of the inspection image 223. As a result, the recognizability of an image pasted in the inspection report 230 can be improved.

It should be noted that the steps of each flow chart herein may be executed in different order, some of the steps may be executed at the same time, or the steps may be executed in different order every time, unless such modifications are contrary to the nature of the processing.

The present invention is not limited to the aforementioned embodiments, and a variety of variations and modifications can be made without departing from the gist of the present invention.

What is claimed is:

1. A reproducing apparatus comprising:
a recording medium reading/writing portion to and from which a recording medium is attachable and detachable and that retrieves a moving image file recorded on the recording medium;
a graphic generating portion that generates an indicator indicating a gravity direction of a distal end portion of an endoscope insertion portion from gravity information data included in the moving image file; and
an image combining portion that displays on a display portion a first combined image obtained by combining endoscope image data included in the moving image file and the indicator indicating the gravity direction generated by the graphic generating portion,
wherein:
the graphic generating portion generates an indicator indicating an insertion length of the distal end portion from data of an insertion length included in the moving image file,
the image combining portion displays on the display portion a second combined image obtained by combining the endoscope image data, the indicator indicating the gravity direction, and an indicator indicating the insertion length of the distal end portion,
the moving image file includes a header portion storing flag information indicating whether or not data of the gravity information and the insertion length information is stored, and
the reproducing apparatus further comprises a control portion that controls the display portion to display the endoscope image or one of the first combined image and the second combined image depending on the flag information stored in the header portion.

2. The reproducing apparatus according to claim 1, wherein:
a plurality of images are recorded on the recording medium reading/writing portion, and
the reproducing apparatus comprises a display control portion that rotates each of the plurality of images based on gravity information on each of the plurality of images so that gravity directions of the plurality of images point downward, and displays the images on the display portion as a list.

3. The reproducing apparatus according to claim 2, wherein the display control portion rotates an image whose gravity direction is an upper half direction 180 degrees based on gravity information on each of the plurality of images, and displays the images on the display portion as a list.

4. The reproducing apparatus according to claim 2, wherein the display control portion displays an indicator indicating a skyward direction and/or a groundward direction in a background of each of the plurality of images based on gravity information on each of the plurality of images, and displays the images on the display portion as a list.

5. The reproducing apparatus according to claim 2, wherein the plurality of images are a plurality of still images, or a plurality of moving image frames in the moving image file.

6. A displaying method comprising:
retrieving a moving image file recorded on a recording medium;
generating an indicator indicating a gravity direction of a distal end portion of an endoscope insertion portion from gravity information data included in the moving image file;
displaying on a display portion a first combined image obtained by combining endoscope image data included in the moving image file and the generated indicator indicating the gravity direction;
generating an indicator indicating an insertion length of the distal end portion from data of an insertion length included in the moving image file; and
displaying on the display portion a second combined image obtained by combining the endoscope image data, the indicator indicating the gravity direction, and an indicator indicating the insertion length of the distal end portion,
wherein the moving image file includes a header portion storing flag information indicating whether or not data of the gravity information and the insertion length information is stored, and
wherein the method further comprises controlling the display portion to display the endoscope image or one of the first combined image and the second combined image depending on the flag information stored in the header portion.

* * * * *